(12) United States Patent  
Jensen et al.

(10) Patent No.: US 7,153,822 B2  
(45) Date of Patent: Dec. 26, 2006

(54) COMPOSITIONS AND METHODS FOR MODULATING CONNEXIN HEMICHANNELS

(75) Inventors: Peter Holme Jensen, Copenhagen (DK); Bjarne Due Larsen, Brønshøj (DK); Lars Bo Laurenborg Hansen, Herlev (DK); Jørgen Søberg Petersen, Hellebæk (DK); Soren Neve, Lyngby (DK); Morten Schak Nielsen, Ballerup (DK); Eddi Meier, Værløse (DK); Eva Steiness, Hellerup (DK)

(73) Assignee: Wyeth, Madison, NJ (US)

( * ) Notice: Subject to any disclaimer, the term of this patent is extended or adjusted under 35 U.S.C. 154(b) by 164 days.

(21) Appl. No.: 10/353,549

(22) Filed: Jan. 29, 2003

(65) Prior Publication Data

US 2004/0092429 A1  May 13, 2004

Related U.S. Application Data

(60) Provisional application No. 60/352,717, filed on Jan. 29, 2002.

(51) Int. Cl.  
*A01N 38/17* (2006.01)  
*A61K 38/00* (2006.01)

(52) U.S. Cl. ............................................. 514/2

(58) Field of Classification Search ............... None  
See application file for complete search history.

(56) References Cited

U.S. PATENT DOCUMENTS

| | | | |
|---|---|---|---|
| 3,740,438 A | 6/1973 | Cook et al. ............... 424/319 |
| 3,862,113 A | 1/1975 | Riniker et al. ........... 260/112.7 |
| 4,340,592 A | 7/1982 | Adibi ........................ 424/177 |
| 4,636,492 A | 1/1987 | Kettner et al. ............ 514/18 |
| 4,652,552 A | 3/1987 | Kettner et al. ............ 514/18 |
| 4,666,890 A | 5/1987 | Kitaura et al. ............ 514/18 |
| 4,797,471 A | 1/1989 | Teetz et al. ............... 514/18 |
| 5,037,957 A | 8/1991 | Grubb et al. ............. 530/330 |
| 5,047,401 A | 9/1991 | Lipsky et al. ............. 514/19 |
| 5,061,710 A | 10/1991 | Haslanger et al. ........ 514/266 |
| 5,206,221 A | 4/1993 | Lipsky et al. ............. 514/19 |
| 5,223,486 A | 6/1993 | Gordon et al. ........... 514/18 |
| 5,252,560 A | 10/1993 | Myers et al. ............. 514/19 |
| 5,432,159 A | 7/1995 | Repolles Moliner et al. . 514/18 |
| 5,446,023 A | 8/1995 | Pavia et al. .............. 514/12 |
| 5,492,894 A | 2/1996 | Bascom et al. ........... 514/18 |
| 5,492,916 A | 2/1996 | Morriello et al. ......... 514/318 |
| 5,492,920 A | 2/1996 | Chen et al. .............. 514/323 |
| 5,494,919 A | 2/1996 | Morriello et al. ......... 514/323 |
| 5,514,694 A | 5/1996 | Powers et al. ............ 514/357 |
| 5,534,538 A | 7/1996 | Drauz et al. ............. 514/19 |
| 5,543,397 A | 8/1996 | Drauz et al. ............. 514/19 |
| 5,602,102 A | 2/1997 | Thiele et al. ............. 514/19 |
| 5,610,297 A | 3/1997 | Powers ..................... 544/168 |
| 5,622,973 A | 4/1997 | Morriello et al. ......... 514/318 |
| 5,637,564 A | 6/1997 | Pavia et al. .............. 514/8 |
| 5,643,955 A | 7/1997 | Kurtz et al. .............. 514/561 |
| 5,650,393 A | 7/1997 | Pavia et al. .............. 514/12 |
| 5,650,508 A | 7/1997 | Powers ..................... 544/168 |
| 5,798,442 A | 8/1998 | Gallant et al. ............ 530/330 |
| 5,811,387 A | 9/1998 | Simon et al. ............. 514/2 |
| 5,849,711 A | 12/1998 | Tung et al. ............... 514/19 |
| 5,872,101 A | 2/1999 | Munoz et al. ............ 514/18 |
| 5,877,182 A | 3/1999 | Nargund et al. .......... 514/278 |
| 5,980,913 A | 11/1999 | Penney .................... 424/278.1 |
| 6,017,925 A | 1/2000 | Duggan ................... 514/300 |
| 6,136,787 A | 10/2000 | Black et al. ............. 514/18 |
| 6,162,828 A | 12/2000 | Fukuda et al. ........... 514/564 |
| 6,187,906 B1 | 2/2001 | Gluckman et al. ....... 530/331 |
| 6,235,929 B1 | 5/2001 | Powers ..................... 562/450 |
| 6,251,625 B1 | 6/2001 | Bommarius et al. ...... 435/68.1 |
| 6,255,285 B1 | 7/2001 | Kotake et al. ............ 514/18 |
| 6,291,640 B1 | 9/2001 | Bailey et al. ............. 530/330 |
| 6,342,481 B1 | 1/2002 | Leoni et al. .............. 514/18 |
| 6,353,023 B1 | 3/2002 | Larsen et al. ............ 514/533 |
| 6,358,978 B1 | 3/2002 | Ritzeler et al. ........... 514/319 |
| 6,384,272 B1 | 5/2002 | Stammler et al. ........ 562/443 |
| 6,410,585 B1 | 6/2002 | Larsen et al. ............ 514/424 |
| 6,780,848 B1 | 8/2004 | Gluckman et al. ....... 514/18 |
| 6,888,022 B1 | 5/2005 | Audia et al. ............. 560/155 |
| 2001/0020006 A1 | 9/2001 | Hans-Ulrich et al. ..... 514/19 |
| 2002/0049164 A1 | 4/2002 | Demuth et al. .......... 514/19 |
| 2002/0169133 A1 | 11/2002 | Dankwardt et al. ...... 514/18 |
| 2003/0050247 A1 | 3/2003 | Kuhner et al. ........... 514/16 |
| 2003/0092609 A1* | 5/2003 | Larsen et al. ............ 514/9 |
| 2003/0092634 A1 | 5/2003 | Buysse et al. ............ 514/18 |
| 2003/0105165 A1* | 6/2003 | Griffith .................... 514/651 |

(Continued)

FOREIGN PATENT DOCUMENTS

CA       2156618       10/1994

(Continued)

OTHER PUBLICATIONS

Lampe et al. Regulation of Gap Junctions by Phosphorylation of Connexins. Archives of Biochemistry and Biophysics. Dec. 15, 2000. vol. 384. No. 2, pp. 205-215.*

(Continued)

*Primary Examiner*—Bruce R. Campell  
*Assistant Examiner*—Marcela M Cordero Garcia  
(74) *Attorney, Agent, or Firm*—Fitzpatrick, Cella, Harper & Scinto

(57) ABSTRACT

Disclosed are compositions and methods for modulating hemichannel function in a cell, tissue or organ. The invention also relates to useful screens for detecting such compounds, particularly those capable of modulating connexin phosphorylation. Further provided are therapeutic methods for preventing or treating conditions impacted by undesired hemichannel function in a mammal such as heart arrhythmia.

4 Claims, 13 Drawing Sheets

U.S. PATENT DOCUMENTS

| | | | |
|---|---|---|---|
| 2003/0114387 A1 | 6/2003 | Castro Pineiro et al. | 514/17 |
| 2003/0135023 A1 | 7/2003 | Demuth et al. | 530/329 |
| 2003/0194445 A1 | 10/2003 | Kuhner et al. | 424/622 |
| 2003/0202989 A1* | 10/2003 | Collier et al. | 424/236.1 |
| 2003/0228353 A1 | 12/2003 | Cowsar | 424/445 |
| 2004/0005304 A1 | 1/2004 | Brudnak | 424/93.45 |
| 2004/0029796 A1 | 2/2004 | Szeto et al. | 514/12 |
| 2004/0092429 A1* | 5/2004 | Jensen et al. | 514/2 |
| 2004/0102609 A1 | 5/2004 | Chatterjee et al. | 530/330 |
| 2004/0106560 A1 | 6/2004 | Sundstrom et al. | 514/19 |
| 2004/0121964 A1 | 6/2004 | Madar et al. | 514/19 |
| 2004/0127427 A1 | 7/2004 | Powers et al. | 514/19 |
| 2004/0142876 A1 | 7/2004 | Colarusso et al. | 514/18 |
| 2004/0167106 A1 | 8/2004 | Rodriguez et al. | 514/167 |
| 2004/0167201 A1 | 8/2004 | Sharma et al. | 514/422 |
| 2004/0171555 A1 | 9/2004 | Demuth et al. | 514/18 |
| 2004/0235752 A1 | 11/2004 | Pitt et al. | 514/19 |
| 2005/0020482 A1* | 1/2005 | Phipps et al. | 514/2 |
| 2005/0059608 A1 | 3/2005 | Jarvinen et al. | 514/19 |
| 2005/0075280 A1* | 4/2005 | Larsen et al. | 514/9 |
| 2005/0107308 A1 | 5/2005 | Posposilik et al. | 514/19 |
| 2005/0113293 A1* | 5/2005 | Larsen et al. | 514/9 |

FOREIGN PATENT DOCUMENTS

| | | |
|---|---|---|
| DE | 41 22 885 A1 | 1/1993 |
| DE | 43 14 260 A1 | 11/1994 |
| DE | 198 16 932 A1 | 10/1999 |
| WO | 93/14777 | 8/1993 |
| WO | 94/03468 | 2/1994 |
| WO | 94/12181 | 6/1994 |
| WO | 94/14817 | 7/1994 |
| WO | 94/15908 | 7/1994 |
| WO | 95/13069 | 5/1995 |
| WO | 96/19494 | 6/1996 |
| WO | WO 9621674 A1 * | 7/1996 |
| WO | 96/30395 | 10/1996 |
| WO | 96/33209 | 10/1996 |
| WO | 97/05889 | 2/1997 |
| WO | 98/10653 | 3/1998 |
| WO | 98/31359 | 7/1998 |
| WO | 99/11606 | 3/1999 |
| WO | 99/31049 | 6/1999 |
| WO | WO 00/75286 | 12/2000 |
| WO | 01/00610 A1 | 1/2001 |
| WO | WO 01/62775 | 8/2001 |
| WO | 01/90085 A1 | 11/2001 |
| WO | 01/92236 A1 | 12/2001 |
| WO | 02/077017 A2 | 10/2002 |
| WO | WO 02/077017 | 10/2002 |
| WO | 02/101007 A2 | 12/2002 |
| WO | 2004/028466 A2 | 4/2004 |
| WO | 2004/048400 A1 | 6/2004 |

OTHER PUBLICATIONS

Actions of the antiarrythmic peptide AAP10 on intercellular coupling. Naunyn Schmiedebergs Arch Pharmacol. Jul. 1997; vol. 356, No. 1., pp. 76-82.*

A. C. Campos de Carvalbo, et al., "Conduction Defects And Arrhythmias In Chagas' Disease: Possible Role Of Gap Junctions And Humoral Mechanisms", Journal of Cardiovascular Electrophysiology, vol. 5, No. 8, Aug. 1994, pp. 686-698.

R. R. Kaprielian, et al., "Downregulation Of Immunodetectable Connexin43 And Decreased Gap Junction Size In The Pathogenesis Of Chronic Hibernation In The Human Left Ventricle", Circulation 97, 1998,pp. 651-660.

N. S. Peters, et al. "Reduced Content Of Connexin43 Gap Junctions In Ventricular Myocardium From Hypertrophied And Ischemic Human Hearts", Circulation, vol. 88, No. 3, Sep. 1993, pp. 864-875.

J. E. Saffitz, et al. "Mechanisms Of Remodeling Of Gap Junction Distributions And The Development Of Anatomic Substrates Of Arrhythmias", Cardiovascular Research 42 (1999) pp. 309-317.

Bruzzone, R. et al. "Connections With Connexins: The Molecular Basis Of Direct Intercellular Signaling", Eur. J. Biochem. 238, pp. 1-27 (1996).

Darrow, B. J. et al. "Expression Of Multiple Connexins In Cultured Neonatal Rat Ventricular Myocytes", Circulation Research, vol. 76, (3), (1995), 18 pages.

Wang, Y. et al. "Inhibition Of Glycosylation Induces Formation Of Open Connexin-43 Cell-to-Cell Channels And Phosphorylation And Triton X-100 Insolubility Of Connexin-43", The Journal Of Biological Chemistry, vol. 270, No. 44, Nov. 3, 1995, pp. 26581-26585.

Yamanaka, I. et al. "Changes In The Phosphorylation States Of Connexin43 In Myoepithelial Cells Of Locating Rat Mammery Glands", European Journal Of Cell Biology, vol. 72, pp. 166-173 (Feb. 1997).

Kondo et al. "Metabolic Inhibition Activates A Non-Selective Current Through Connexin Hemichannels In Isolated Ventricular Myocytes", J. Mol. Cell. Cardiol. 32, pp. 1859-1872 (2000).

Li, F. et al. "Activation Of Connexin-43 Hemichannels Can Elevate [Ca2+]1 And [Na+]1 In Rabbit Ventricular Myocytes During Metabolic Inhibition", J. Mol. Cell. Cardiol. 33, pp. 2145-2155 (2001).

Beardslee, M. A. et al. "Dephosphorylation And Intracellular Residtribution Of Ventricular Connexin43 During Electrical Uncoupling Induced By Ischemia", Circ. Res. 87, pp. 656-662, Oct. 13, 2000.

Lin, R. et al. "v-Src Phosphorylation Of Connexin 43 On Tyr247 And Tyr265 Disrupts Gap Junctional Communication", The Journal Of Cell Biology 154 (4), pp. 815-827 (2001).

Mohammad Z. Hossain, et al. "Regulation Of Cx43 Gap Junctions: The Gatekeeper And The Password", (published Oct. 17, 2000) Science's Stke, Perspective, five pages.

Tomoko Nao, et al. "Alteration Of Gap Junction Proteins Connexin40 and 43 In Atrial Myocardial Tissue In Patients With Chronic Atrial Fibrillation", Abstract from American Heart Associations Annual Meeting, Anaheim, California, Nov. 2001, one page.

Alexandre F. Stewart, et al. "Hypophosphorylation Of Connexin40 Mediates Conduction Disease In RTEF-1 Transgenic Mice", Abstract from American Heart Associations Annual Meeting, Anaheim, California, Nov. 2001, one page.

Sawa Kostin, et al.. "Structural Correlate Of Atrial Fibrillation In Human Hearts", Abstract from American Heart Associations Annual Meeting, Anaheim, California, Nov. 2001, one page.

Weisheng Bao, et al. "Signaling Mechanisms Involved In Atrial Tachycardia-Induced Remodeling Probed In An Isolated, Perfused Rabbit Heart Model", Abstract from American Heart Associations Annual Meeting, Anaheim, California, Nov. 2001, one page.

Shigeto Kanno, et al. "Effects Of Diminished Connexin43 Expression On Infarct Size And Arrhythmias In Mice With Developing And Healed Myocardial Infarcts", Abstract from American Heart Associations Annual Meeting, Anaheim, California, Nov. 2001, one page.

Masaya Tanno, et al. "Blockade Of Gap Junction Communication During The Early Period Of Ischemia Protects Cardiomyocytes From Infarction", Abstract from American Heart Associations Annual Meeting, Anaheim, California, Nov. 2001, one page.

Knütter, et al., "Analysis of the Transport Properties of Side Chain Modified Dipeptides at the Mammalian Peptide Transporter PEPT1", European Journal of Pharmaceutical Sciences 21 (2004) 61-67.

Wang, et al. (Cardiovasc Res. Jul. 2002; 55(1):25-37.Review).

Henriques JP et al. (Eur Heart J Jul. 2002; 23(14):1112-1117).

Kwak BR, et al. (Molec Biol Cell; 2001: 12, 831-845).

Eugenin , EA, et al. (Proc. Natl. Acad. Sci. USA; 2001; 98, 4190-4195).

Alford A et al. (Am J Physiol Lung Cell Mol Physiol 2001; 208: L680-L688).

Cai W-J, et al. (J Mol Cell Cardiol 2001; 33: 957-967).

Wang H-Z, et al. (Am J Physiol Cell Physiol. 2001; 281: C75-88).

Schuster A, et al. (Am J Physiol Heart Circ Physiol. 2001; 280: H1088-H1096).

Melman A, Christ JC (Urol Clinic North America. 2001: 28: 217-231).
Hashitani H, et al. (J Physiol 2001; 530: 273-286).
Wang H-Z, et al. (Urology. 2001; Suppl. (6A): 111).
Oviedo-Orta E, et al. (FASEB. 2001; 15:768-774).
Meier, E and Beck, M M: (2001 International Gap Junction Conference, Aug. 4-9, 2001, Hawaii, USA (Abstract No. 132)).
Teilman, S.C, et al.: (2001 International Gap Junction Conference, Aug. 4-9, 2001, Hawaii, USA (Abstract No. 176)).
Pitre DA, et al. (Neurosci Lett. 2001; 303: 67-71).
Todt I, et al. (J Membrane Biol. 2001;181: 107-114).
Masuda M, et al. (Anat Rec. 2001; 262; 137-146).
Vitale ML, et al. (Biol Reporo. 2001; 64: 625-633).
Haefliger J-A, et al. (Kidney Int. 2001; 60: 190-201).
Fukumoto M, et al. (Life Sciences. 2001; 69:247-254).
Murakami S, Muramatsu T (Anat Embryol. 2001; 203: 367-374).
Nadya Lumelsky et al. in Differentiation of Embryonic Stem Cells to Insulin-Secreting Structures Similar to Pancreatic Islets. Science, 292, 1389-1394, 2001.
Orlic et al. (Nature 410, 701-705 (2001)).
Kyung-Sun Kang, et al. (Cancer Letters 2001; 166, 147-153).
Saunders MM, et al. (Cancer Res. 2001; 61: 1765-1767).
Oku H, et al. (Invest Ophthalmol Vis Sci. 2001; 142: 1915-1920).
Zhou ZY, et al. (Neuroscience 2001; 102: 959-967).
Lagostena L, et al. (J Physiol 2001; 531: 693-707).
Quist AP, et al. (J. Cell Biol. 2000; 148: 1063-1074).
Cotrina ML, et al. (J Neurosci 2000; 20(8): 2835-2844).
Hansson L, et al. (Nutrition and Cancer, 2000; 36 No. 1, 122-128).
Ashino Y, et al. (Am J Physiol Lung Mol Physiol 2000; 279: L5-L13).
Christ GJ, (Int J Import Res. 2000; 12 Suppl. 4: s15-25).
Oviedo-Orta E, et al. (Immunology 2000; 99: 578-590).
Blasits S, et al. (Phlugers Arch. 2000; 440: 710-712).
Dürig J, et al. (Brit J Haematol. 2000; 111: 416-425).
Colwell C, (J Neurobiol. 2000; 43: 379-388).
Shinohara K, et al. (Neurosci Lett. 2000; 286: 107-110).
Hagendorff, A et al. (Circulation 1999; 99: 1508).
Stevens RJ, et al. (Am J Physiol. 1999; 2777: C448-C460).
Abdullah KM, et al. (Endocrine. 1999; 10: 35-41).
Sakagami K, et al. (J Physiol (Lond). 1999; 521: 637-650).
Levy D, et al. (Neurosci Lett. 1999; 260: 207-209).
Carmeliet, E., Cardiac Ionic Currents and Acute Ischemia: From Channels to Arrhythmias. (Physiol Rev., 1999, 79: 917-1017).
Simon AM, et al. (Curr Biol 1998; 8: 295-298).
Cotrina ML, et al. (Proc Natl Acad. Sci. USA 1998; 95:15735-15740).
Do Carmo A, et al. (Exp Eye Res. 1998; 67: 569-572).
Wright AR, Rees SA, (Pharmacol Ther. 1998; 80(1): 89-121. Review).
Gupta P, et al. (Blood. 1998; 91: 3724-3733).
Guerineau NC, et al. (J Biol Chem. 1998; 273: 10389-10395).
Yoshida M, et al. (Arch Toxicol. 1998; 72: 192-196).
Chen X, et al. (Chem Biol Interact 1998; 111-112: 263-275).
Peters, NS, Wit, AL., Myocardial Architecture and Ventricular Arrhythmogenesis. (Circulation 1998; 97: 1746-1754).
Nicolson GI, et al. (Proc. Natl Acad Sci USA. 1998; 85: 473-476).
Guerrero, PA, et al. (J Clin Invest 1997; 99: 1991-1998).
Polacek D, et al. (J Vasc Res 1997; 34: 19-30).
Yeh H-I, et al. (Arterioscle Thromb Vasc Biol 1997; 17: 3174-3184).
Rehman J, et al. (AM J Physiol 1997; 272: H1960-H1971).
Turner WH, Brading AF. (Pharmacol Therap. 1997; 75: 77-110).
Bruzzone R, Ressot C. (J Eur Neurosci. 1997; 9: 1-6).
Kumar, N, Gilula, NB. (Cell 1996; 84: 381-388).
Christ GJ, et al. (Circ Res. 1996; 79:631-646).
Nagy JI, et al. (Cell Growth Diff. 1996; 7: 745-751).
Bolaños, JP, Medina JM. (J Neurochem. 1996; 66: 2019-2099).
Kohner EM, et al. (Diabetes 1995; 44: 603-607).
Wolburg H, Rohkmann A. (Int Rev Cytol 1995; 157: 315-373).
Endo K, et al. (J Gastroenterol Hepatol. 1995; 10: 589-594).
Bény J-L, et al. (Physiol Heart Circ Physiol 1994; 266: H1465-H1472).
Charash WE, et al. (Am Rev Respir Dis 1993; 148: 467-476).
Bursell S-V, et al. (Curr Eye Res. 1992; 11: 287-295).
Bennett M, et al. (Neuron 1991; 6: 305-320).
Low PA, Nickander, KK. (Diabetes 1991; 40: 873-877).
Rosendaal M, et al. (Tissue Cell 1991; 23: 457-470).
Petersen JS, et al. (J Pharmacol. Esp. Ther. 1991; 258: 1-7).
Klaunig JE, Ruch RJ. (Lab Investigation 1990; 62 No. 2: 135-146).
Johnstone BM, et al. (J Physiol 1989; 408: 77-92).
Torikata C, et al. (Lab Invest 1985; 52: 399-408).
Iguchi Y, et al. (Arch Oral Biol. 1984; 29: 489-497).
L Form, cf. (Pure & Appl. Chem. 1984; vol. 56(5): 595-624).
Lynch JJ, et al. (J Cardiovasc. Pharmacol. 1981; 3: 49-60. Mice (25-30 g)).
Taugner R, Schiller A. (Cell Tissue Res. 1980; 206: 65-72).
König, W, Volk, A, "Succinimidbildung bei der Synthese des Insulin-A-Ketten (14-21)-Octapeptids", (Engegangen am 31. Mars. 76).
Cunha-Vaz JG, et al. (Br J Ophthalmol. 1975; 59: 649-56).

* cited by examiner

|           |   |   |   |   |   |   |   | 244 |   |   | 247 |   |   |   |
|-----------|---|---|---|---|---|---|---|-----|---|---|-----|---|---|---|
|           | V | K | D | R | V | K | G | R S | D | P | S   | H | A | T |

|     | PKA       |
|-----|-----------|
|     | PKC       |
|     | PKG       |
|     | CaMk 11   |
|     | Tyr Kinase|
|     | MAPN      |

*: p<0.05 versus MI Vehicle

I.p. infusion dose of Compound 1

COMPOSITIONS AND METHODS FOR MODULATING CONNEXIN HEMICHANNELS

CROSS-REFERENCE TO RELATED APPLICATION

The present application is a continuation-in-part of U.S. Provisional Application Ser. No. 60/352,717 as filed on Jan. 29, 2002, the disclosure of which is hereby incorporated by reference.

FIELD OF THE INVENTION

The present invention generally relates to compositions and methods for modulating connexin hemichannels. The invention also relates to useful screens for detecting such compounds.

BACKGROUND

There is recognition that gap junctions are important plasma membrane structures that help cells communicate with their environment. For example, most gap junctions are thought to assist passage of small molecules and ions between interconnected cells. Such movement is believed to exert profound effects on many aspects of cell physiology. Plasma membranes of adjacent cells are believed to include hemichannels, "connexons", formed by multimeric proteins called "connexins" that help form the gap junctions. In addition, hemichannels play an independent role in the exchange of small molecular weight compounds between the cell cytoplasm and the periplasmic or extracellular space. See generally Bennett, M. et al. (1991) *Neuron* 6: 305; Kumar, N. and Gilula, N. B. (1996) *Cell* 84: 381; and Quist, A. P et al (2000) *J. Cell Biol*. 148: 1063 and references cited therein.

In particular, there have been reports that many gap junctions are specialized regions of the cell membrane with clusters of densely packed channels. Such gap junction channels are thought to directly connect the cytoplasmic compartment of two neighbouring cells.

There is recognition that gap junction channels are composed of two hemichannels (connexons) provided by each of two neighbouring cells. Each connexon (hemichannel) has been disclosed as consisting of six proteins called connexins. Each connexin is thought to share four transmembrane domains, two extracellular loops, and a cytoplasmic loop. The conduction of the electrical impulse is thought to take place through the gap junctions, thereby facilitating normal heart conduction and rhythm. See generally P. A. Guerrero, R. B. et al. *J Clin Invest* 1997, 99 1991; D. L. Lerner, K. A. et al., *Circulation* 1999, 99 1508; S. Kirchhoff, E. et al. *Curr Biol* 1998, 8 295.

Distribution of most heart connexins is thought to vary significantly throughout the organ. It has been disclosed that the Cx43 isoform is a major ventricular type while Cx40 is the most abundant isoform in the atrias and conductive system.

There are reports of strong links between connexin abnormalities and heart disease. See A. C. de Carvalho, et al., *J Cardiovasc Electrophysiol* 1994, 5 686; R. R. Kaprielian, et al., *Circulation* 1998, 97 651; N. S. Peters, et al., *Circulation* 1993, 88 864; and J. E. Saffitz, R. B. et al., *Cardiovasc Res* 1999, 42 309.

There is understanding that abnormal expression, distribution and regulation of gap junctions are involved in arrhythmias. The antiarrhythmic peptides disclosed by Larsen, B. et al. in PCT/DK01/00127 (WO01/62775) have been reported to increase gap junction intercellular communication (GJIC) in vertebrate tissue.

Particular mammalian gap junction proteins encoded by the connexin (Cx) gene family have been reported. See Bruzzone, R. et al. (1996) *Eur. J. Biochem*. 238: 1. The Cx family includes Cx26, 30, 31, 32, 37, 40, 43, 45, 46 and 50. Gap junction channels have also been found in invertebrates, where the channel forming proteins are called "innexins"

There is understanding that most connexins may be phosphorylated except for the Cx26 protein. The Cx43 protein is widely expressed in tissues. There are reports that phosphorylation of the Cx43 protein effects gap junction intracellular communication (GJIC). For example, there is acknowledgement that Cx43 turn over, trafficking, phosphorylation and gating are impacted by phosphorylation. See Darrow, B. J., et al. (1995). *Circ Res* 76: 381.

For example, Saffitz and co-workers have shown using conductance measurements that during ischemia there is an increase in connexin serine dephosphorylation within 15 minutes. See FIG. 1 (showing a mammalian Cx43 transmembrane protein with several identified phosphorylation sites).

The phosphorylation and solubility of the connexins has attracted research interest. In particular, Cx43 was found to be phosphorylated in the myoepithelial cells of rat mammary glands. See Wang, Y., et al. (1995). *J Biol Chem* 270, 26581; and Yamanaka, I., et al. (1997). *Eur J Cell Biol* 72: 166.

As mentioned, gap junction channels are thought to be specialized pores that connect the cytoplasm of neighboring cells. Hemichannels communicate with the extracellular environment. There have been reports that metabolic inhibition of heart cells can activate an influx pathway that may be structured by connexin hemichannels. Metabolic inhibition is thought to open the hemichannel and enhance loss of potassium, and induce influx of protons, sodium and calcium, thereby damaging heart tissue. See Kondo et al *J. Mol. Cell. Cardiol*. 32:1859–72, 2000; Li et al *J. Mol. Cell. Cardiol*. 33: 2145–55, 2001).

Electrical uncoupling at gap junctions during acute myocardial ischemia is believed to contribute to conduction abnormalities and reentrant arrhythmias. Increased levels of intracellular $Ca^{2+}$ and $H^+$ and accumulation of amphipathic lipid metabolites during ischemia promote uncoupling. Other mechanisms may play a role. For instance, it has been reported that uncoupling induced by acute ischemia is associated with changes in phosphorylation of connexin43 (Cx43). Results have been reported that are consistent with rapid, reversible Cx43 dephosphorylation playing a role in myocardial uncoupling and arrhythmogenesis during acute ischemia. See Beardslee M A et al., *Circ Res*. 2000;87:656 and references cited therein.

The structure and function of hemichannels have attracted interest.

For example, atomic force microscopy (AFM), fluorescent dye uptake assay, and laser confocal immunofluorescence imaging, have suggested that hemichannels are involved in extracellular calcium-dependent modulation of cell volume. As reported, cell volume changes were dependent on whether or not connexin43 was expressed. Changes were reported to be preventable by gap-junctional blockers (e.g., oleamide and beta-glycyrrhetinic acid) or were reversed by returning extracellular calcium to normal. It was suggested that nongap-junctional hemichannels regulate cell volume in response to the change in extracellular physiological calcium in an otherwise isosmotic situation. See Quist, A. P. et al, supra.

It has been proposed that open hemichannels, especially during ischemia or metabolic stress, may lead to cellular uptake of $Ca^{2+}$, protons and accumulation of amphipathic lipid metabolites in cells causing cellular swelling, cell damage or apoptosis. See Beardslee et al., supra and Quist et al. supra.

There have been reports Cx43 is phosphorylated a positions Tyr247 (Y247), Tyr265 (Y265) and perhaps other positions by the activated Src protein in vitro. Significantly, gap junction intercellular communication (GJIC) was reported to be resistant to disruption by phosphorylation mediated by v-Src. It was acknowledged that phosphorylation on Y247 and Y265 of Cx43 is important. See Lin R, et al. (2001) *J Cell Biol* 154(4):815. See also FIG. 1.

See also Larsen, B. D et al. in a PCT application entitled *New Medical Uses of Intracellular Communication Facilitating compounds* as filed on 22 Feb. 2002 as PCT/US02/05773 (WO 02/077017) in which a variety of GJIC modulating compounds have been disclosed.

It would be desirable to have compounds that modulate hemichannel function. Preferred compounds would assist opening or closing of the hemichannel. It would be especially desirable to have molecular screens to identify such compounds.

SUMMARY OF THE INVENTION

The invention generally features compounds and methods of using same to modulate hemichannel function. Particular compounds modulate hemichannel phosphorylation. Additional compounds of the invention modulate hemichannel function and in some instances also impact gap junction communication (GJIC) eg., by opening or closing gap junction channels. Useful screens for detecting and characterizing such compounds are also provided. The invention has many useful applications including providing therapies to treat or prevent various conditions modulated by unsuitable hemichannel function.

There is an urgent need to identify compounds that modulate (increase or decrease) hemichannel function. By "hemichannel function" is meant the opening or closing of connexin hemichannels to enhance or decrease passage of molecules or ions through the hemichannel. By the phrase "gap junction function" is meant the opening or closing of gap junctions to increase or reduce passage of molecules or ions through the gap junction. Preferred invention compounds modulate hemichannel phosphorylation and, typically also help open or close the hemichannel. Hemichannel function and gap junction function can be readily detected and optionally quantified by one or more of the standard assays disclosed herein.

More specific hemichannel modulating compounds modulate (increase or decrease) phosphorylation of a recognized connexin. Preferred sites of phosphorylation or dephosphorylation include one or more of a tyrosine, serine or threonine residue on the connexin. As will be discussed below, it has been found that modulation of phosphorylation on one or more of these residues impacts hemichannel function, particularly by opening and closing the hemichannel. Thus, and as described below, it is an object of the invention to provide screens adapted to monitor the phosphorylation state of the connexins as a means of detecting and optionally characterizing compounds with capacity to modulate hemichannel function.

For instance, certain compounds according to the invention are capable of phosphorylating at least one tyrosine residue of the connexin. In this embodiment, phosphorylation of the connexin will help close the hemichannel. Other suitable hemichannel modulating compounds decrease phosphorylation (dephosphorylate) at least one serine residue of the connexin. In this example, dephosphorylation of the serine will help open the hemichannel. Still other compounds within the scope of the invention will enhance phosphorylation of at least one threonine residue of the connexin, typically to assist in the closure of the hemichannel. Additionally suitable invention compounds facilitate at least one of: an increase or decrease in serine phosphorylation, an increase or decrease in tyrosine phosphorylation, and an increase or decrease in threonine phosphorylation of the connexin. Preferably, one or more of the amino acid modifications will assist in a detectable opening or closing of the hemichannel.

Accordingly, and in one aspect, the invention provides a method to modulate hemichannel function preferably by closing the hemichannel. In one embodiment, the method involves closing the hemichannel in a cell, tissue or organ preferably exposed to stress including contacting the stressed cell, tissue or organ with a therapeutically effective amount of at least one of the compounds represented below as Formula I or II. Preferred contact according to this method embodiment is sufficient to close the hemichannel before, during or after exposure to the stress relative to a suitable control. Examples of such stress include one or more of metabolic inhibition, oxygen deprivation, lowering pH, or increasing extracellular potassium ion as described below.

In a more specific embodiment, the method further includes monitoring phosphorylation of a recognized connexin, preferably connexin 43 (Cx 43). Typically, the method will detect and report any increase or decrease in Cx43 phosphorylation on at least one of a tyrosine, serine, and threonine reside thereon, preferably an increase in phosphorylation in at least one of tyrosine and threonine. In this embodiment, the method also includes closing the hemichannel and, optionally, opening or closing gap junction channels relative to a suitable control.

The invention provides other methods to modulate hemichannel function. In one embodiment, the method involves monitoring phosphorylation of a recognized connexin, preferably Cx43, to detect any increase or decrease in Cx43 phosphorylation on at least one of a tyrosine, serine and threonine residue thereon, preferably a decrease in phosphorylation of one or more of those residues such as serine relative to a control. In this invention example, the method involves opening the hemichannel in a cell, tissue or organ exposed to stress including contacting the stressed cell, tissue or organ with a therapeutically effective amount of at least one of the compounds represented below as Formula I or II. Preferred contact is sufficient to open the hemichannel and, optionally, open or close gap junction channels relative to a suitable control.

There is a need for screens to detect and characterize such hemichannel modulating compounds more specifically. Having such screens would be an important first step toward identifying and characterizing a range of new hemichannel modulating compounds e.g., by in vitro testing of a candidate compound relative to a control to detect capacity to help close hemichannels, for instance, by at least 5% more than a control compound. compounds identified by such a screen, including the compounds represented below as Formula I or II, can be used to in therapies that promote cell, tissue and organ homeostasis, for instance, by preventing, reducing or protecting against loss of cellular components to the extracellular environment.

Accordingly, the present invention also provides specific in vitro methods for screening candidate compounds that have capacity to modulate hemichannel function. Typically, the method involves contacting suitable cells, tissue or an organ with at least one compound represented below as Formula I or II. Preferably, the contact is under conditions conducive to modulating phosphorylation of a recognized connexin, preferably connexin 43 (Cx43) and detecting a change in Cx43 phosphorylation relative to a suitable control. Also preferably, the change in phosphorylation is taken to be indicative of a hemichannel modulating compound. Optionally, such compounds detected by the screening method may open or close gap junction channels according to assays disclosed herein.

In each of the foregoing methods, preferred phosphorylation changes according to the invention occur almost entirely at or near the intracellular C-terminus of the connexin. More preferred sites of phosphorylation and dephosphorylation of Cx43 are shown in FIG. 1. By the phrase "C-terminus of connexin" is meant the region spanning about amino acid residues 240 to 281 as shown in FIG. 1.

A particular in vitro screening assay of the invention for detecting connexin phosphorylation involves one or more steps designed to monitor hemichannel function, gap junction function (or both). Such an assay generally includes at least one and preferably all of the following steps:
  1) culturing a population of cells, a tissue or an organ such as those derived from the heart or muscle,
  2) stressing the cells, tissue or the organ preferably by oxygen deprivation or metabolic inhibition,
  3) adding a known or candidate hemichannel modulating compound such as those represented by Formula I or II below,
  4) detecting a change in connexin phosphorylation (preferably Cx 43) relative to a suitable control; and
  5) optionally measuring the change as being indicative of a compound that modulates hemichannel function and optionally gap junction function.

That assay can effectively measure capacity of the hemichannel modulating compound to increase or decrease phosphorylation of at least one of a serine, tyrosine and threonine residue of the preferred Cx43 protein. Reference herein to a "standard in vitro connexin phosphorylation assay" or related phrase refers to the above protocol of steps 1) through 5). The assay can be conducted with nearly any population of primary, secondary, or immortalized cells such as those derived from heart or muscle.

The foregoing standard in vitro assay is generally flexible. For instance, steps 1)–5) can be performed in nearly any order provided intended screening results are achieved. Thus in one embodiment of the assay, the candidate compound is added at step 1), step 2) (or both steps) instead of after step 2) exclusively.

The present invention provides other methods for screening candidate compounds for capacity to modulate hemichannel function. In one embodiment, the method includes contacting suitable cells, tissue or an organ with at least one compound selected from the group represented below as Formula I or II. Typically, any uptake of a detectable reporter by the cells, tissues or organ is monitored in the presence of the compound and relative to a suitable control. Preferred detectable reporters have a molecular size that is conducive to passage through an open hemichannel. Thus, when the hemichannel is open in the assay, the detectable reporter enters the cell, tissue or organ. However when the hemichannel is closed, the detectable reporter is prevented from passing through the hemichannel. The contact is preferably under conditions conducive to detecting any change in the uptake of the detectable reporter with reference to a suitable control.

A hemichannel is "closed" in accord with the invention if at least one of the tyrosine residues in the C-terminal region of connexin, preferably Cx43 is phosphorylated, preferably at least the tyrosine at position 247 or position 265, more preferably both of same, as detected for instance in the standard in vitro connexin phosphorylation assay. By "closed" is also meant at least one of the threonine residues in the C-terminal region of the connexin is phosphorylated, which residues may be phosphorylated alone or in addition to tyrosine phosphorylation. A hemichannel is "open" if at least one of the serine residues in the C-terminal region of the connexin is dephosphorylated. Additionally preferred tyrosine, threonine and serine residues are shown in FIG. 1 as kinase sites.

A more specific in vitro screening assay for detecting passage of the detectable reporter through the hemichannel involves one or more of the following steps:
  1) culturing a population of cells, a tissue or an organ such as those derived from the heart or muscle,
  2) stressing the cells, tissue or the organ preferably by oxygen deprivation or metabolic inhibition such as by adding a glucose derivative,
  3) adding a known or candidate hemichannel modulating compound such as those represented below by Formula I or II,
  4) adding a detectable reporter such as a fluorescent, chemiluminescent, or phosphorescent compound such as fluorescent dye such as calcein and related compounds,
  5) detecting a change in uptake of the detectable reporter into the cells, tissue or organ relative to a suitable control; and
  6) optionally measuring the change as being indicative of a compound that modulates hemichannel function.

That assay can effectively measure capacity of the candidate compound to open or close hemichannels in the cells, tissue or organ which change is readily detectable microscopically by visualizing the detectable reporter. Reference herein to a "standard in vitro uptake assay" or related phrase refers to the above protocol of steps 1) through 6). The assay can be conducted with nearly any population of primary, secondary, or immortalized cells such as those derived from heart or muscle. Other acceptable reports include suitable radioactive compounds also having a size permitting passage through the hemichannel. Particular compounds include those labeled with one or more of the following radionuclides: $^3H$, $^{35}S$, and $^{14}C$.

Importantly, the standard in vitro uptake assay described generally above is not bound to any particular order of steps so long as intended assay results are achieved. Thus in one embodiment, at least one of the candidate compound and detectable reporter of steps 3) and 4), respectively, are added individually or together before step 2) in the method. In this example of the assay, the cells, tissue or organ is stressed in the presence of the compound and the detectable reporter. Alternatively, the detectable reporter can be "loaded" into the cells at step 1) to detect compounds with capacity to open hemichannels.

The invention provides further methods for screening one or more candidate compounds for capacity to modulate hemichannel function. In one embodiment, the method includes contacting cells, tissue or an organ with at least one compound selected from those represented by Formula I or II below. Typically, the cells, tissue or organ is loaded with a detectable reporter to measure volume. Preferred detectable reporters for use in the assay have a molecular size that is suited for passing through an open hemichannel. The contact is preferably under conditions conducive to detecting any change in the volume of the cells, tissue or organ as registered by the detectable reporter and by referring to a suitable control. Preferably, the cells, tissue or organ is stressed and the candidate compound closes the hemichannel so that cell volume is maintained or decrease more slowly when compared to a suitable control.

One particular in vitro screening assay for detecting cell volume changes involves one or more of the following steps:
1) culturing a population of cells, a tissue or an organ such as those derived from the heart or muscle,
2) loading the cells, tissue or organ with a detectable reporter such as a fluorescent, chemiluminescent, or phosphorescent compound such as dye, such as calcein or a related compound,
3) estimating the volume of the cells, tissue or organ by detecting and quantifying signal from the detectable reporter,
4) adding a known or candidate hemichannel modulating compound such as those represented by Formula I or II below,
5) stressing the cells, tissue or the organ preferably by oxygen deprivation or metabolic inhibition such as by adding a glucose derivative,
6) detecting a change in cell volume relative to a suitable control; and
7) optionally measuring the change as being indicative of a compound that modulates hemichannel function and optionally gap junction function.

The assay can effectively measure capacity of the candidate hemichannel modulating compound to open or close hemichannels in the cells, tissue or organ by observing cell volume changes microscopically. Reference herein to a "standard in vitro cell volume assay" or related phrase refers to the above protocol of steps 1) through 7). The assay can be conducted with nearly any population of primary or secondary cells derived from heart or muscle such as cardiomyocytes and related cells or tissue.

The standard in vitro cell volume assay is not bound to any particular order of steps so long as intended assay results are achieved. Thus in one embodiment, the candidate compound of step 4) is added after stressing the cells in step 3) to monitor ability of the compound to close hemichannels in already stressed cells as exemplified by a slower rate of cell volume decrease. Thus in one embodiment of the assay, a change in the rate of cell volume decrease or increase is monitored over a pre-determined time frame. However in another embodiment, the cell volume change can be monitored at a fixed time point e.g., at a time between about 1 to 120 minutes after stressing the cells, tissue or organ.

As discussed, the in vitro assays of the invention are flexible and can be adapted to suit an intended screening use. For instance, a particular candidate hemichannel modulating compound, such as those represented by Formula I or II below, can be employed as the sole active agent or in combination with other agents including other compounds to be tested. In most, but not all instances, the in vitro assays are performed with reference to a suitable control assay usually including the same or closely related test conditions as in the steps above, but without adding the compound to be tested to the culture medium. In such cases, a candidate hemichannel modulating compound can be identified by exhibiting at least 2% greater activity in the assay relative to the control, more preferably at least about 5% greater activity relative to the control assay, and still more preferably at least about 10% or greater activity, eg., about 20% to about 40% relative to the control assay.

As discussed, particular hemichannel modulating compounds will also impact gap junction channels. For instance, certain compounds may help close the hemichannels and assist in the opening of gap junction channels. However, other compounds may help open the hemichannels while assisting in the closure of gap junction channels. Still other compounds may open both hemichannels and gap junctions while others may close gap junctions and hemichannels.

Accordingly, the invention also provides a method of increasing gap junction intracellular communication (GJIC) in a cell, tissue or organ. In one embodiment, the method involves administering a therapeutically effective amount of at least one compound selected those represented by Formula I or II as described below. Preferably, the contact is sufficient to increase the GJIC in the cell, tissue or organ relative to a suitable control.

Also provided are combinations of in vitro assays in compounds are selected for capacity to modulate hemichannels and gap junctions. In one embodiment, at least one of the standard in vitro connexin phosphorylation assay, the standard in vitro uptake assay, and the standard in vitro cell volume assay, is combined with one or more of the GJIC assays disclosed by Larsen, B. et al. in a PCT application entitled *Novel Antiarrhythmic Peptides* as filed on 22 Feb. 2001 as PCT/DK01/00127 (WO 01/62775) or as disclosed by Larsen, B. et al. in another PCT application entitled *New Medical Uses of Intracellular Communication Facilitating compounds* as filed on 22 Feb. 2002 as PCT/US02/05773 (WO 02/077017). Examples of such suitable GJIC assays include those measuring cell conductance by patch clamp, calcium wave measurements and dye transfer assays. The disclosures of the PCT/DK01/00127 (WO 01/62775) and PCT/US02/05773 (WO 02/077017) applications are hereby incorporated by reference.

By way of illustration and not limitation, the standard in vitro connexin phosphorylation assay described above is employed to select one or more hemichannel modulating compounds. One or more of the compounds can subsequently be further screened in the cardiomyocyte patch clamp assay described in the PCT/US02/05773 (WO 02/077017) application. compounds providing suitable activity in both assays will have capacity to modulate hemichannels and gap junctions.

The invention further provides in vivo testing of the candidate hemichannel modulating compounds to help detect and optionally quantify therapeutic capacity to modulate a heart arrhythmia. As discussed, it is believed that most heart arrhythmias can be prevented, alleviated or treated by use of one or a combination of the compounds of this invention. A preferred in vivo testing model, referred to herein as a "standard in vitro mouse arrhythmia assay" or related phrase, has been disclosed in PCT/DK01/00127 (WO 01/62775) as well as in PCT/US02/05773 (WO 02/077017). Certain compounds according to the invention will desirably prolong the time until onset of induced atrial ventricular (AV) block by at least about 20% (score of at least 2) in the assay. Other compounds will exhibit a prolongation of at least about 60% or the time until onset of the induced AV block (score of at least 3) in the assay. In broad terms, the assay involves administering one or more compounds to a suitable mouse, injecting calcium chloride to induce arrhythmia, and detecting the time of onset of the arrhythmia (preferably 2$^{nd}$ degree AV-block) compared to a suitable control.

Significantly, use of multiple detection formats (ie., a combination of at least one of the standard in vitro assays and the in vivo arrhythmia assay as disclosed herein) can efficiently perform multiple analyses, thereby enhancing the accuracy and probability of identifying a hemichannel modulating compound (as represented by Formulae I and II, for instance) with good therapeutic capacity. This feature of the invention is especially useful when large numbers of compounds are to be tested. For example, some or nearly all of the compounds according to Formula I or II can be tested. Alternatively, or in addition, suitable compounds could be made by standard synthetic methods including combinatorial-type chemical manipulations and then tested in accord with the invention.

In embodiments in which multiple detection formats are practiced, it is important to note that significant in vitro and in vivo activity as determined by the assays described herein is not a required feature of a hemichannel modulating compound. That is, certain compounds described herein will exhibit good activity in at least one of the standard in vitro assays described herein but will not exhibit significant activity in the standard in vivo arrhythmia assay. Alternatively, certain other compounds will exhibit significant activity in the in vivo arrhythmia assay but will not show good activity in one or more of the standard in vitro assays. However, a preferred hemichannel modulating compound will exhibit good activity in at least one of the in vitro and in vivo assays described in this application.

Compounds showing good activity in the standard in vivo arrhythmia assay will sometimes be called "antiarrhythmic compounds" or like phrase to denote capacity to prolong time to arrhythmia in the assay.

As will be discussed in more detail below, compounds of the invention can be used to prevent or treat a wide spectrum of medical conditions that are associated or suspected of being related to undesired or abnormal passage of molecules and/or ions through cell membranes. For instance, nearly all the medical indications disclosed in PCT/DK01/00127 (WO 01/62775) and PCT/US02/05773 (WO 02/077017) can be addressed in this way. Some of said medical indications are disclosed herein. The medical indications may be prevented, alleviated or treated by using one or a combination of compounds disclosed in the present application and particularly those showing good activity in at least one of the in vitro and in vivo assays provided herein.

Additional compounds suitable for testing and use with the present invention have been disclosed by Larsen, B. D et al. in PCT/US02/05773 (WO 02/077017).

In another aspect, the invention provides a method of preventing or treating tissue or organ stress in a mammal. In one embodiment, the method includes administering a therapeutically effective amount of at least one compound selected from the group of compounds represented by Formulae I and II above. Preferably, the contact is sufficient to prevent or treat the stress in tissue or organ.

The invention also provides for a method of treatment of burns comprising administering to a patient in need of such treatment a therapeutically effective amount of a compound that blocks connexin hemichannel opening.

Also provided is a method of treatment of thromboses. In one embodiment, the method includes administering to a patient in need of such treatment a therapeutically effective amount of a compound that blocks a connexin hemichannel from opening.

In another aspect, the invention also features a method of treatment of respiratory and metabolic acidosis. In one embodiment, the method includes administering to a patient in need of such treatment a therapeutically effective amount of a compound that blocks a connexin hemichannel from opening.

The invention also provides for a method of treatment of focal arrhythmia. In one example of the method, it includes administering to a patient in need of such treatment a therapeutically effective amount of a compound that blocks a connexin hemichannel from opening.

Further provided by the invention is a method of treating and preventing cell and tissue damage resulting from elevated levels of blood glucose. In one embodiment, the method includes administering to a patient in need of such treatment a therapeutically effective amount of a compound that blocks a connexin hemichannel from opening.

The invention also features a method of treatment of chronic atrial fibrillation. In one embodiment, the method includes administering to a patient in need of such treatment a therapeutically effective amount of a compound that blocks a connexin hemichannel from opening.

Also provided is a method of treatment of epilepsia. Typically, the method includes administering to a patient in need of such treatment a therapeutically effective amount of a compound that promotes a connexin hemichannel to open.

Further provided is a method of cytoprotecting tissue or an organ of a mammal in need of such treatment, the method comprising administering a therapuetically effective amount of at least one compound selected from the group consisting of the compounds represented by Formula I or II.

The invention also provides for a method of preventing or treating reperfusion injury in a mammal, the method comprising administering a therapuetically effective amount of at least one compound selected from the group consisting of the compounds represented by Formula I or II.

In each of the foregoing therapeutic methods, a compound according to the invention that features good anti-arrhythmic activity as determined by the standard in vitro mouse arrhythmia assay (ie., score of at least 2). Such compounds will sometimes be referred to herein as "antiarrhythmic" compounds or a related phrase.

Further uses and advantages of the present invention will be apparent from the following discussion and examples. Other aspects of the invention are also discussed below

BRIEF DESCRIPTION OF THE DRAWINGS

FIG. 1 (SEQ ID NO: 1) is a drawing showing phosphorylation sites on a connexin (Cx43). As can be seen, the cytosolic domain of the Cx43 transmembrane protein has several potential serine and tyrosine phosphorylation sites.

FIG. 3A shows results from compound 1 administration. FIG. 3B shows results from administration of compound 1 and compound 2.

FIG. 7A: Cardiomyocytes under light microscopy; FIG. 7B: Fluorescence under control conditions (same as cells in FIG. 7A); FIG. 7C Fluorescence after 30 minutes of metabolic inhibition.

FIG. 9A Relative volume during metabolic inhibition in the presence or absence of compound 1 (0.1 nM). FIG. 9B shows control data.

DETAILED DESCRIPTION OF THE INVENTION

Figure 2:
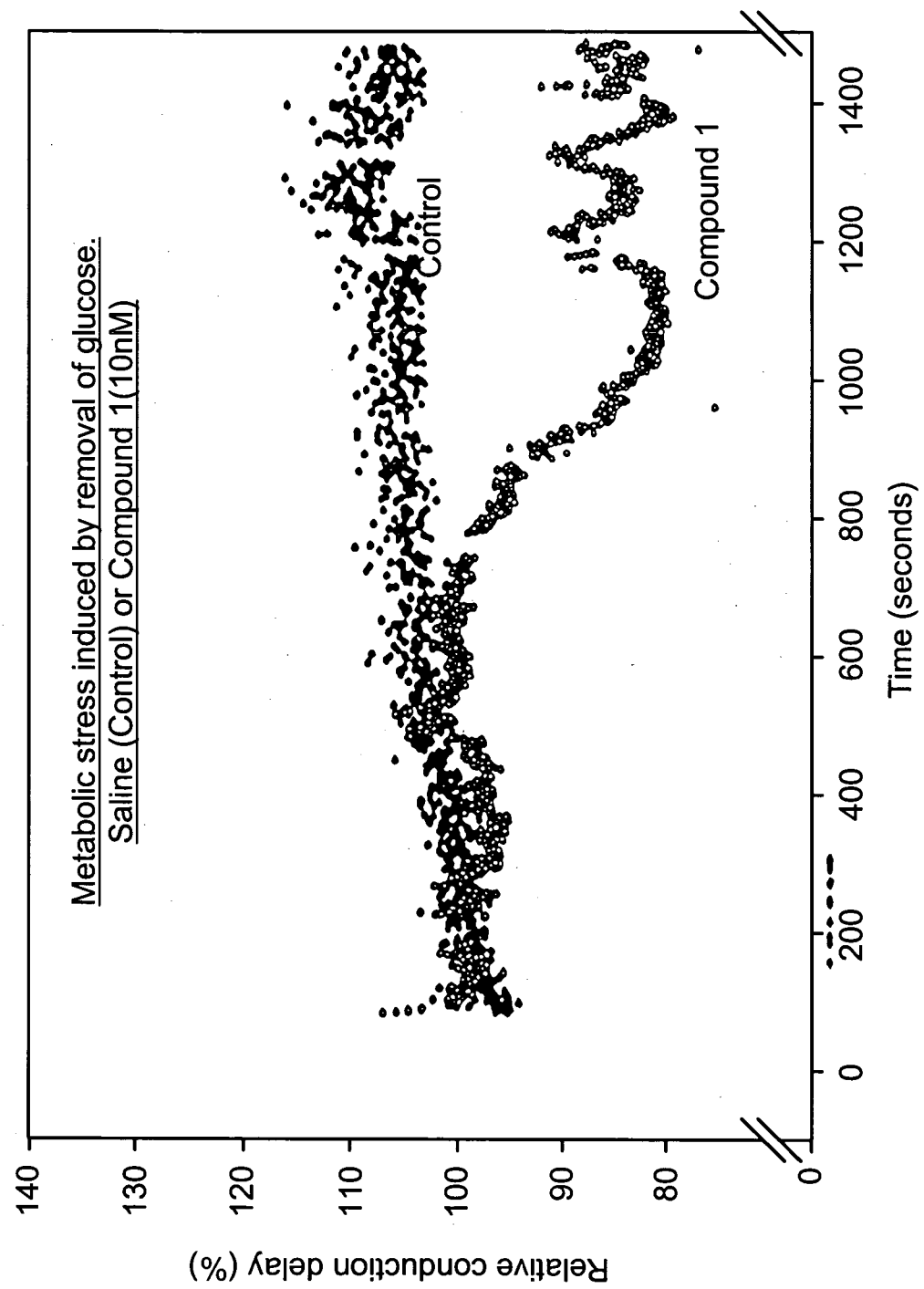
FIG. 2 is a graph showing metabolic stress induced by removal of glucose. As can be seen from the graph, administration of compound 1 reduces the stress as evidenced by a decrease in relative conduction delay.

As discussed, the invention provides compounds and methods of using same to modulate hemichannel function. More particular compounds modulate hemichannel phosphorylation to assist opening or closing of hemichannel. Useful screens for detecting and characterizing such compounds are also provided which screens include in vitro assays, an in vivo assay, or a combination thereof. Further provided are therapeutic methods useful for the treatment or prevention of conditions impacted by unsuitable hemichannel function.

It is an object of the invention to demonstrate, for the first time, that cell, tissue and organ stress may be adversely impacted by the closing and opening of hemichannels. Without wishing to be bound to theory, it is believed that metabolic stress, such as oxygen deprivation during ischemia, glucose deprivation, uncoupling of the oxidative phosphorylation caused by HCN, or uncoupling of the citric acid cycle, may all contribute to uncoupling of the intercellular gap junctional communication (GJIC). It is further believed that this uncoupling is correlated with modulation of connexin phosphorylation, more particularly dephosphorylation of connexin-tyrosine residues and/or connexin-serine residues and/or threonine residues in the gap junction channel. By way of illustration, it is believed that during atrial fibrillation, the atrial cells have increased metabolic demand due to the high frequency pacing. This is thought to lead to lactate acidosis, opening of hemichannels and uncoupling of gap junctions.

It is also an object of this invention to provide methods of modulating hemichannel function and, optionally, gap junction intercellular communication (GJIC) which methods include contacting cells, tissue or organs with a therapeutically effective amount of one or a combination of compounds that have such activity. Preferred compounds have been disclosed in the PCT/DK01/00127 (WO 01/62775) and PCT/US02/05773 (WO 02/077017) by B. Larsen et al.

More preferred compounds suitable for use with the present invention include those represented by the following Formula I:

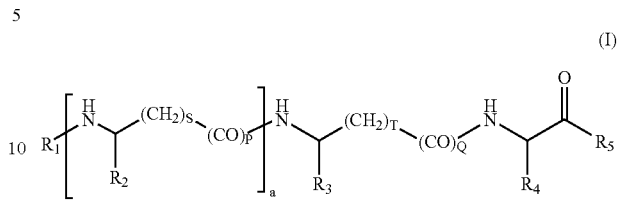

wherein
R1 represents H or acetyl (Ac)
R2 represents a sidechain of one of the amino acids G, Y, D-Y, F and D-F,
R3 represents any amino acid sidechain R4 represents a sidechain of one of the amino acids G, Y, D-Y, F and D-F,
R5 represents OH1 or NH2
and a, S, T, P and Q are integers are integers and independently=0 or 1;

and salts thereof.

More specific compounds include those having the following Formula II:

R1-X1-X2-X3-R2  (II)

wherein,
X1 is 0, Ala, Gly, B-Ala, Tyr, D-Tyr, Asp,
X2 is 0; Ala-Gly-T4c-Pro; Ala-Sar-Hyp-Pro; Ala-Asn; D-Asn-D-Ala; D-Asn; Gly, Ala; D-Ala; B-Ala; Asn; or;
X3 is Tyr; D-Tyr; Gly, or Phe; and
R1 is H or Ac, with the proviso that X1 and X2 are not both 0; and salts thereof.
R2 is OH or NH2

More specific compounds represented by Formula I or II above include the following: G-(DBF)-Y-NH$_2$, H-GA-Sar-Hyp-PY-NH$_2$, H-GAG-T4c-PY-NH$_2$, Gly-Ala-Asn-Tyr, D-Tyr-D-Asn-D-Ala-Gly, D-Tyr-D-Asn-Gly, Gly-Gly-Tyr, Gly-Ala-Tyr, D-Tyr-D-Ala-Gly, Gly-D-Asn-Tyr, Gly-βAla-Tyr, βAla-βAla-Tyr, Gly-βAla-Phe, Gly-Asn-Phe, Asn-Tyr, Ac-Gly-Tyr, Ac-Ala-Tyr, (reduced Gly)-Gly-Tyr(H$_2$N—CH$_2$—CH$_2$—NH—CH$_2$—C(O)-Tyr).

Other compounds in accordance with the present invention include:

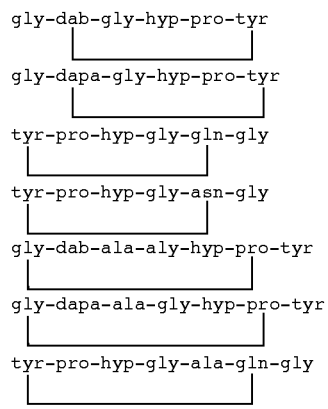

-continued

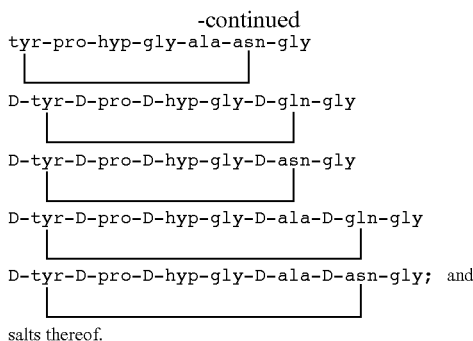

salts thereof.

Additionally preferred candidate compounds of the invention feature an oral bioavailability of more than about 5% as determined by an acceptable oral bioavailability assay.

Generally preferred assays involve intraduodenal administration of a candidate components to a suitable test subject. Availability of the compounds in a biological sample, preferably a blood sample, is then detected and preferably quantified.

Further preferred candidate compounds generally satisfy Lipinski's rule of 5. As applied, it defines bioavailability. According to the Rule, less than satisfactory adsorption is more likely when one or more of the following features characterizes a particular candidate compound: 1) More than 5 H-bond donors (expressed as the sum OH's and NH's), 2) Molecular weight over 500, 3) Log P is over 5, 4) More than 10 H-bond acceptors (expressed as sum of N's and O's), and 5). Two parameters out of range are to be avoided for many invention embodiments.

Still further preferred compounds in accord with the invention are relatively stable in blood plasma. An acceptable assay involves contacting a desired candidate compound with plasma (rodent, rabbit or primate serum, for instance), incubating the compound with the plasma, and then detecting and preferably quantifying stability of that compound over time. Preferred plasma sources are rats, dogs, cats, mice, pigs, cows, horses, and humans. A preferred assay, sometimes referred to herein as "standard plasma stability assay" has been disclosed in the PCT application PCT/US02/05773 (WO 02/077017). Typical compounds giving good activity in the assay feature C-terminal amidation or esterification, use of D-amino acids and derivatives of natural amino acids, N-terminal modifications, and the cyclic structures. One or a combination of such modifications can enhance stability while retaining substantial biological activity.

Especially preferred hemichannel modulating compounds for use with the present invention include: Ac-D-Tyr-D-Pro-D-4Hyp-Gly-D-Ala-Gly-NH2 (compound 1); Ac-Gly-Asn-Tyr-NH2 (compound 2); and salts thereof.

Figure 1:
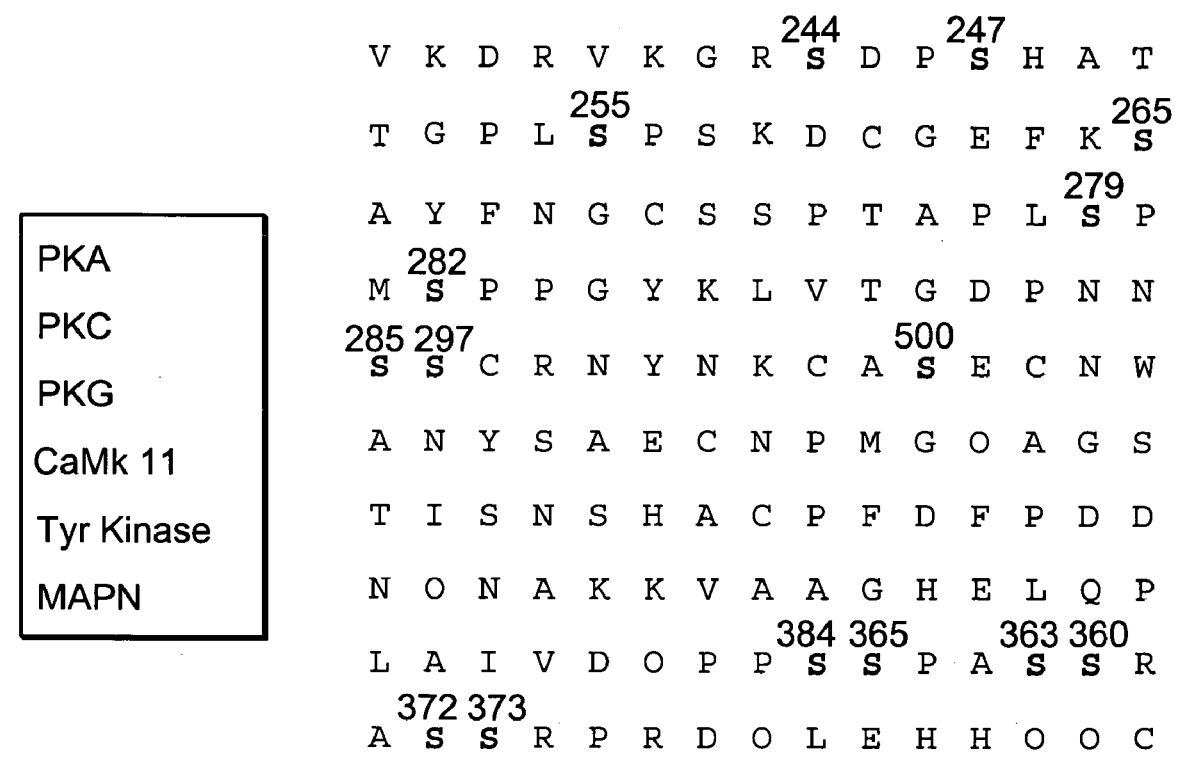

Preferred hemichannel modulating compounds exhibit significant activity in one or a combination of the standard in vitro and in vivo assays disclosed herein. Such compounds also have capacity to close or open hemichannels and, optionally, to modulate GJIC. Preferably, a suitable compound enhances or reduces phosphorylation of connexin 43 (Cx43) as determined by the standard in vitro connexin phosphorylation assay. A more specific assay monitors phosphorylation and/or dephosphorylation of one or more of the tyrosine, serine and threonine amino acid residues shown in FIG. 1. A more particular assay format follows.

1) culturing a population of about $10^5$ cells in medium such as confluent or semi-confluent rat cardiomyocytes or H9c2 cells,
2) stressing the cells by washing same and subsequently culturing them in glucose poor medium for about an hour or less,
3) adding compound 1 to the medium to a concentration of about 0.1 to about 200 nM for about 10 minutes to eight hours,
4) lysing the cells and then detecting a change in Cx 43 tyrosine, serine, and/or threonine phosphorylation relative to a suitable control; and
5) measuring the change in phosphorylation as being indicative of a compound that modulates hemichannel function.

In one embodiment of the method, the detecting step 4) further comprises testing the candidate compound in an immunological or cell sorting-based assay. In cases in which an immunological assay is employed that assay will typically include contacting cells with the candidate compound under conditions sufficient to increase or decrease phosphorylation of the connexin. Preferably, the method further includes producing a lysate of the cells; and detecting increased or decreased connexin phosphorylation in the cell lysate. That increase or decrease is taken to be further indicative of the hemichannel modulating compound.

Preferred immunological assays for use with the method have been described and include immunoprecipitation assays, antibody capture assays, two-antibody sandwich assays, antigen capture assays, radioimmunoassays (RIAs) and the like. See generally E. Harlow and D. Lane in Antibodies: *A Laboratory Manual*, Cold Spring Harbor Laboratory (1988); Ausubel et al. (1989) in *Current Protocols in Molecular Biology*, J. Wiley & Sons, New York for a discussion relating to many standard immunological methods, the disclosures of which are incorporated herein by reference.

A preferred immunological assay is an ELISA assay. Thus in one embodiment, the forgoing method further includes at least one and preferably all of the following steps:
a) coating a solid support with a first antibody that specifically binds the connexin, preferably connexin 43 (Cx43),
b) contacting the cell lysate to the solid support under conditions conducive to forming a binding complex between the first antibody and the connexin,
c) contacting the first antibody:connexin binding complex with a second antibody, the contacting being under conditions sufficient to form a specific binding complex between the second antibody and any phosphorylated connexin in the first antibody:connexin binding complex,
d) contacting the first antibody:connexin:second antibody binding complex with a detectably-labeled third antibody that binds the second antibody; and
e) detecting presence of the third detectably-labeled antibody on the solid support as being further indicative of the compound.

In one embodiment of the method, the third antibody of the method is detectably-labeled with at least one of biotin, FITC, TRITC, radioactive iodine or peroxidase. In another embodiment, the second antibody is an anti-phosphotyrosine antibody. In still another embodiment, the second antibody is an anti-phosphoserine antibody. In some instances, detection of the detectably-labeled third antibody is performed by radio- or gama scintillation counting.

In another embodiment, the immunological method employed as the detecting step is a radioimmunoassay (RIA). Preferably, such an RIA includes at least one and preferably all of the following steps:
a) detectably-labeling the cells before producing the cell lysate, wherein the labeling is under conditions conducive to labeling phosphorylated connexin, preferably connexin 43 (Cx43),
b) contacting the cell lysate with an antibody that forms a specific binding complex with the connexin,
c) separating the binding complex from the detectably-labeled cell lysate; and
d) detecting the labelled and phosphorylated connexin as being further indicative of the gap junction modulating compound.

In one embodiment of the method, the antibody is an anti-connexin antibody. In another embodiment, the detection step further comprises performing a Western immunoblot assay. The RIA method is compatible with a wide range of detectable labels however for many applications administration of radioactive inorganic phosphorous will be preferred.

Antibodies for use with the foregoing invention method including anti-phosphotyrosine, anti-phosphoserine, and anti-Cx43 antibodies are commercially available from a variety of sources such as the American Type Culture Collection (ATCC); Sigma Chemical Co., St. Louis, Mo.; Zymed Lab, Inc., of California; and Amersham Biosciences, U.K.

Preferred hemichannel modulating compounds identified by the foregoing standard in vitro test show good capacity to modulate phosphorylation of Cx43, particularly at one or more of the tyrosine, serine and threonine residues shown in FIG. 1. More preferred of such compounds exhibit at least a 5% change in such phosphorylation (measured as an increase of decrease in the presence of one or more of phosphotyrosine, phosphoserine, and/or phosphothreonine on Cx43), preferably at least about 10%, more preferably at least about 50% change relative to stressed cells in which the compound is present at a concentration of between about 0.1 nM to about 200 nM.

See Examples 2–5 below for a particular example of the standard in vitro connexin phophorylation assay.

As discussed, the invention also features a standard in vitro uptake assay that can be used to detect and optionally characterize hemichannel modulating compounds. The assay can be used alone or in combination with the standard in vitro connexin phosphorylation assay. A particular embodiment of the standard in vitro uptake assay is described as follows.
1) culturing a population of about $10^5$ confluent rat ventricular myocytes in medium,
2) stressing the cells by replacing the medium with glucose poor medium for less than about 2 hours, preferably about 30 minutes,
3) adding compound 1 to the medium to a concentration of about 0.01 pM to 100 nM,
4) adding calcein dye to the medium to a concentration of about 10 to about 500 micromolar for less than about 2 hours and preferably about 30 minutes,
5) detecting a change in uptake of the calcein into the cells; and
6) measuring the change as being indicative of a compound that modulates hemichannel function.

The step of detecting the change in calcein uptake can be performed by one or a combination of standard methods including fluorescent light microscopy and/or related cell sorting methods. See Example 6 for a particular example of the standard in vitro uptake assay.

Preferred compounds detected by the forgoing standard in vitro uptake assay will exhibit at least about a 5% decrease in dye uptake (close cell hemichannels) relative to stressed cells, preferably at least about a 20% decrease and more preferably at least about a 50% decrease in the presence of between about 0.01 pM to 100 nM of the compound to be tested.

As also discussed, the invention provides the in vitro cell volume assay which assay can be alone or in combination with one or both of the standard in vitro connexin phosphorylation and the standard in vitro uptake assay. A particular embodiment of the standard in vitro cell volume assay is as follows.
1) culturing a population of about 1 confluent rat ventricular myocytes in medium,
2) loading the cells with between from about 0.5 to about 100 micromolar calcein-AM, preferably about 5 micromolar, for less than about 2 hours and preferably about 15 minutes
3) estimating the volume of the cells by detecting and preferably quantifying signal from the calcein-AM,
4) adding compound 1 to the medium to a concentration of about 0.01 nM to about 100 nM,
5) stressing the cells by culturing in glucose poor medium,
6) detecting a change in cell volume relative to a suitable control; and
7) measuring the change as being indicative of a compound that modulates hemichannel function.

The step of detecting the change in cell volume can be performed by one or a combination of standard methods including laser confocal microscopy and/or related cell sorting methods. Example 7 provides a particular example of the standard in vitro cell volume assay.

Preferred compounds detected by the forgoing standard in vitro cell volume assay will exhibit at least about a 5% decrease in cell volume (close hemichannels) relative to stressed cells, preferably at least about a 20% decrease and more preferably at least about a 50% decrease in the presence of between about 0.01 nM to 100 nM of the compound to be tested. Compounds selected in accord with this assay will inhibit flow of osmolytes through hemichannels and help maintain normal cell volume during conditions that produces cellular swelling. Importantly, cell swelling is associated with impaired perfusion in organs surrounded by a fibrous capsule (e.g., heart, kidney, skeletal muscle) or bone (brain, spinal cord) and therefore compounds with hemichannel blocking properties may be useful in the treatment of diseases associated with cellular swelling.

Suitable control experiments are generally tailored for use in a particular assay format. For example, most control experiments involve subjecting a test sample (e.g, a population of cultured rat cardiomyocytes) to non-stressful conditions such as incubation in medium. Typically, water, buffer, phosphate-buffered saline or the like is added to the assay instead of the compound(s) to be tested in parallel or separately. A desired assay is then conducted in accord with the present methods. Specific examples of suitable controls are provided in the Examples section.

Practice of the invention is compatible with a wide spectrum of conventional detection assays. Such assays can be performed manually, semi-manually, or in an automated format as needed. For applications in which rapid or large scale screening strategies are needed, the invention is additionally compatible with standard "high-throughput" and/or "ultra-high throughput" screening methodologies. Examples of such methods include immunological and cell sorting type assays such as those described herein.

As discussed, the present invention is compatible with a wide spectrum of testing strategies. Thus in some embodiments, further testing of candidate compounds will be performed in vivo to test for and preferably confirm hemichannel modifying activity. For instance, one or a combination of the standard in vitro methods described herein can be used to further test compounds for hemichannel modulating activity in the standard in vivo arrhythmia model. The standard in vivo mouse arrhythmia assay, described below as Reference Example 1, has been disclosed in the PCT/DK01/00127 (WO 01/62775) and PCT/US02/05773 (WO 02/077017) by B. Larsen et al.

Candidate compounds identified by one or more of the invention methods have a variety of important applications including use a probes for identifying gap junctions and particularly hemichannels in a range of cells, tissues and organs. Also, such compounds can be used as probes for detecting gap junctions and hemichannels in various developmental and disease states, and as probes for detecting those structures with distinct carbohydrate decoration and/or phosphorylation patterns. Such compounds find further use as solid support components for purifying gap junction components according to standard chromatographic procedures.

Compounds selected by the in vitro and/or in vivo tests described herein can be used as medicaments for preventing or treating conditions impacted by increased opening of hemichannels (increased cell membrane permeability to the extracellular compartments) eg., wounds such as burns, thromboses, respiratory and metabolic acidosis, tissue swelling eg., due to bacterial or environmental toxins, and focal arrhythmias. Other medicaments of the invention can be employed to protect cells from disruptive volume changes. Such changes can be facilitated by one or a combination of factors including excessive heat, ischemia, toxins, inflammation, oedema, disturbance of electrolytes, increased levels of glucose, and diabetic late complications. Treatment of chronic atrial fibrillation associated with increased serine-phosphorylation is also contemplated. Additional compounds can be used as medicaments to prevent, treat, alleviate, or reduce the severity of the following conditions. See also the PCT/DK01/00127 (WO 01/62775) and PCT/US02/05773 (WO 02/077017) application.

The therapeutic methods of the invention generally comprise administration of a therapeutically effective amount of one or a combination of the hemichannel modulating compounds disclosed herein to a subject in need of such treatment, such as a mammal, and particularly a primate such as a human. Treatment methods of the invention also comprise administration of an effective amount of a compound of Formula I or II as defined above to a subject, particularly a mammal such as a human in need of such treatment for an indication disclosed herein.

Typical subjects include mammals suffering from one or a combination of disorders as provided herein including the conditions described below in Sections A–R.

A. Nervous Tissue

It is well known that microglia are the main immune effector of the central nervous system (CNS), and that they are activated in response to a wide range of injuries that trigger brain inflammatory responses, including head injury and ischemia, neurodegenerative diseases, autoimmune diseases, infectious diseases, prion diseases, and brain tumors. Activated microglia migrate to injured CNS areas, where they proliferate and gradually remove cell debris. Eugenin et al showed that microglia can communicate with each other through gap junctions that are induced by inflammatory cytokines (Eugenin, E A, et al. *Proc. Natl. Acad. Sci. USA*, Vol. 98, 4190–4195, 2001). This was demonstrated in the following experiments. At brain stab wounds, microglia progressively accumulated over several days and formed aggregates that frequently showed Cx43 immunoreactivity at interfaces between cells. In primary culture, microglia showed low levels of Cx43 determined by Western blotting, diffuse intracellular Cx43 immunoreactivity, and a low incidence of dye coupling. Treatment with the immunostimulant bacterial lipopolysaccharide (LPS) or the cytokines interferon-gamma (INF-gamma) or tumor necrosis factor-alpha (TNF-alpha) one at a time did not increase the incidence of dye coupling. However, microglia treated with INF-gamma plus LPS showed a dramatic increase in dye coupling that was prevented by coapplication of an anti-TNF-alpha antibody, suggesting the release and autocrine action of TNF-alpha. Treatment with INF-gamma plus TNF-alpha also greatly increased the incidence of dye coupling and the Cx43 levels with translocation of Cx43 to cell-cell contacts. The cytokine-induced dye coupling was reversibly inhibited by 18-glycyrrhetinic acid, a gap junction blocker. Cultured mouse microglia also expressed Cx43 and developed dye coupling upon treatment with cytokines, but microglia from homozygous Cx43-deficient mice did not develop significant dye coupling after treatment with either INF-gamma plus LPS or INF-gamma plus TNF-alpha.

Forced expression of gap junction proteins, connexins, enables gap junction-deficient cell lines to propagate intercellular calcium waves. Cotrina et al. demonstrated that ATP secretion from poorly coupled cell lines, C6 glioma, HeLa, and U373 glioblastoma, is potentiated 5- to 15-fold by connexin expression. These observations indicate that cell-to-cell signaling associated with connexin expression results from enhanced ATP release mediated through connexin hemichannels (Cotrina M L et al. *Proc Natl Acad Sci USA* 1998 Dec. 22; 95(26):15735–40; Cotrina et al.: *J Neurosci* 2000 Apr. 15; 20(8):2835–44). Moreover, during conditions with metabolic stress (e.g., ischemia), hemichannel-mediated ATP release from astrocytes may affect neighboring neurons and elicit elevations in intracellular calcium with in turn may turn in apoptosis and neuronal death.

Due, for instance, to the phosphorylation of Cx43 tyrosine by compound 1 and compound 2, administration of these compounds will assist in hemichannel closing and facilitate the intercellular communication of microglia and thereby augment or speed up the "healing" processes in the aforementioned diseases (brain inflammatory responses, including head injury and ischemia, neurodegenerative diseases, autoimmune diseases, infectious diseases, prion diseases, and brain tumors). Furthermore, it is expected that closing of hemichannels will prevent ATP release and thus reduce spreading of the primary injury.

B. Lung Tissue: Alveolar Cells

Alveolar intercellular communication via gap junctions between alveolar cells is important for the propagation of ion transport, mechanochemical signal transduction, regulation of cell growth and secretion of surfactant factor (Ashino Y, et al. (*Am J Physiol Lung Mol Physiol* 2000; 279: L5–L13)). In vivo repair after acute and chronic inflammatory damage of the alveolar region of the lung involves formation of fibronectin as part of the extracellular matrix (Charash W E, et al. (*Am Rev Respir Dis* 1993; 148:

467–476) and Torikata C; et al. (*Lab Invest* 1985; 52: 399–408)). Alveolar epithelial cell culture studies have demonstrated an increased number of gap junctions in parallel to an increase of extracellular fibronectin concentration (Alford A I, Rannels D E. (*Am J Physiol Lung Cell Mol Physiol* 2001; 280:L680–L688)). In vivo animal studies have found a decreased number of gap junctions after nitrogen dioxide induced severe pulmonary inflammation both in the alveolar tissue, the walls of the terminal bronchioles, alveolar ducts and peribronchiolar alveoli. These findings were dose dependent. However, if pretreated with taurin this loss of gap junctions was prevented in parallel with less pronounced inflammatory reactions. Similar findings were seen after irradiation of rat lung and after treatment with the chemotherapeutic compound, bleomycin.

Thus, maintaining the gap junctional communication in lung tissue is important for preventing lung fibrosis and decreased amount of connexin is seen as a reaction to inflammatory processes, to various toxic stimuli, such as gas inhalation, airborne destructive substance and irradiation. Pretreatment with a compound of the invention that phosphorylates Cx43 tyrosine residues, and facilitates hemichannel closing and/or gap junction opening or gap junctional communication will be indicated prior to therapeutic irradiation where the lungs are exposed, e.g. in lung cancer, treatment of breast cancer, thyroid and esophageal cancers.

Treatment with a compound that facilitates or mediates hemichannel closing and/or gap junction opening will prevent further deterioration of lung function in emphysema, asbestosis, silicosis, lung fibrosis, pneumonitis, drug induced lung fibrosis and in patients exposed to pulmonary toxic gasses such as nitrogen dioxide. Treatment will preferably be added on to conventional treatment of these conditions. The compound may be administered orally, parenterally, nasally, or via pulmonary inhalation.

C. Smooth Muscle

1. Vascular System

Intercellular communication through gap junction channels plays a fundamental role in regulating and modulating vascular myocyte tone throughout the vascular tree (Christ G J, et al. *Circ Res*. 1996; 79: 631–646)). Another important role of gap junction communication is the spread of hyperpolarization among smooth muscle cells involved in vascular relaxation response (Benny J L, et al. *Physiol Heart Circ Physiol* 1994; 266: H1465–72)).

The specialized functions of the endothelium require gap junction intercellular communication between endothelial cells within the monolayer and between endothelium and other cells present in the vessel wall. The communication between these different cell types via gap junctions in coronary capillaries as well as in all other vessels has been documented in several studies. Evidence of involvement in adaptive arteriogenesis has also been demonstrated (Cai W-J, et al. *J Mol Cell Cardiol* 2001; 33: 957–67), Wang H-Z, et al. *Am J Physiol Cell Physiol*. 2001; 281: C75–88), Schuster A, et al. *Am J Physiol Heart Circ Physiol*. 2001; 280: H1088–96)).

In different vascular patophysiological situations where the endothelial monolayer is disrupted as in diet induced hypercholestrolemic lesions the gap junction communication is decreased in the vascular smooth muscles (Polacek D, et al. *J Vasc Res* 1997; 34: 19–30). Injury at the endothelial cellular layer is seen during venous stasis and when thrombophlebitis is developed. Kwak B R, et al. *Molec Biol Cell* 2001; 12: 831–845 has clearly demonstrated that gap junction communication serves to coordinate cell migration during endothelial repair and also are important for capillary sprouting during angiogenesis.

Treatment with compounds of the invention that facilitate hemichannel closing and/or gap junction communication will improve the impaired inter cellular communication in the affected vascular areas, and will be particularly useful during organ ischemia, e.g. claudicatio intermittens and myocardial infarction.

However after baloon catheter injury in rat carotid the vascular healing process is characterised by increased gap junction communication. (Yeh H I, et al. *Arterioscle Thromb Vasc Biol* 1997; 17:3174–84). A suitable invention compound will be administered before the balloon intervention and is preferably an add-on therapy to conventional medical treatment of this condition. Administration of the compound will preferably be parenterally. Effect can be tested in tissue sampled before and at different time after the balloon catheter injury. Faster healing of the endothelial surface will be seen using conventional microscopy. Also improvement of gap junction communication will be found. See also *Arterioscle Thromb Vasc Biol* 1997; 17:3174–84).

2. Erectile Dysfunction

In Corpus cavernosum a syncytial cellular network is established via gap junctions and is critical to erectile function and ensures that the corporal and arterial smooth muscle cells of the penis respond in a uniform and coordinated manner. (Christ G J. (*Int J Impot Res*. 2000; 12 suppl. 4: S15–25), Melman A, Christ J C. (*Urolog Clin North America*. 2001; 28: 217–31)). Disturbed erectile function is seen in diabetes, arteriosclerosis, different neurological diseases and many chronic diseases. From studies in diabetes an inverse correlation between neural innervation and intercellular coupling point towards the potential functional plasticity of the corporal environment although not establishing the functional intercellular communication via gap junction.

Treatment with a compound that facilitates hemichannel closing and/or gap junction opening will improve the communication via the gap junction and thereby normalize the complex coordination between the smooth muscle cells in corpus cavemosum and the vessels.

In vivo pharmacological testing of erectile function of the compounds can be tested 10 weeks after streptozotocin (35 mg/kg i.p.) induced diabetes in rats (8 weeks old) as described by Rehman J, et al. (*Am J Physiol* 1997; 272: H1960–71). Penile reflexes and the intracavernous pressure are measured during local and systemic administration of different doses of the different hemichannel modulating compounds with measures and techniques described by the same research group. An increase in penile reflexes and in the intracavernous pressure of 25% or above can be seen.

Treatment of erectile dysfunction can be administered either locally in the penil corpus, as subcutanous injection or orally. Treatment will be either monotherapy or add-on to conventional treatment of this condition.

3. Incontinence

Smooth muscles in the urine bladder are characterized by phasic contractions and show spontaneous phasic contractions. However the bladder is in the healthy condition able to contain several hundred milliliters of urine without showing an increased intravesical pressure. In contrast to the normal bladder unstable bladders develop spontaneous increases in intravesical pressure related to urge incontinence (Turner W H, Brading A F. (*Pharmacol Therap*. 1997; 75: 77–110). Compared to gastrointestinal smooth muscle, bladder smooth muscles does not spontaneously generate co-ordinated contractions (Stevens R J, et al. (*Am J Physiol*.

199; 2777: C448–60), Hashitani H, et al. (*J Physiol*. 2001; 530: 273–86)). Both electrical and morphological communications via gap junctions between smooth muscle cells in the bladder has recently been demonstrated (Hashitani H, et al. (*J Physiol*. 2001; 530: 273–86), Wang H-Z, et al. (*Urology*. 2001; Suppl 6A: 111)). The importance of these gap junctions was demonstrated by specific inhibition of the communication. Waves of spontaneous excitation in bladder smooth muscle propagate through gap junctions.

The uncontrolled urged incontinence will therefore be regulated via treatment with a hemichannel closing compound or a gap junction opener. Administration will be parenterally, orally or into the urinary bladder. Administration will preferably be as an add-on to treatment with drugs intended to normalize muscle contraction in the urine bladder.

Myoepithelial cells as presented in submandibular glandular ducts, in urether, in gall ducts, pancreatic ducts, tear duct are connected with gap junctions and intercellular communication is essential for the synchronization of contractile function of the myoepithelial cells (Taugner R, Schiller A. (*Cell Tissue Res*. 1980; 206: 65–72). Disturbed contractility in these ducts can be normalized by treatment with a hemichannel closing compound or a gap junction opener administered either parenterally or orally.

D. Healing

Prophylactic effect of treatment with a hemichannel closing agent or gap junction opener, such as compound 1 and compound 2, can be tested in an experimental set up as described by Yeh H I, et al. (*Arterioscle Thromb Vasc Biol* 1997; 17:3174–84). compound 1 or compound 2 can be administered before the balloon intervention using dosages in the range of 10–11 to 10–8 depending upon the compound's biological kinetics, e.g. as determined in the calciumchloride induced arrhythmia model described above. Tissue can be sampled before and at different time after the balloon catheter injury. Faster healing of the endothelial surface will be seen using conventional microscopy. Administration of the compound will be, e.g. parenterally.

Healing progresses in a series of overlapping phases beginning with haemostasis (coagulation). The second phase of the healing process is a cascade of inflammatory responses where microphages accumulates at the wound side and formulation of granulation tissue starts involving fibroblast and lymphocytes among other component. Epithelial cells will then start to migrate from the border of the wound to cover the area. Capillary spouting from the normal tissue into the wound is also involved in order to ensure supply of nutrients, oxygen and the different cells. All the cells and the capillary endothelium cells have an lively intercellular communication via gap junctions (Abdullah K M, et al. (*Endocrine*. 1999; 10: 35–41). Areas with low oxygen supply and/or high concentration of free radicals often seen in wounds with necrotic tissue, in diabetes, in arteriosclerosis, in surgery wounds, oedema, infection, burn wounds and in venous insufficiency will lower the gap junction communication (Nagy J I, et al. *Cell Growth Diff*. 1996; 7: 745–51)).

Treatment with a hemichannel closing compound or a gap junction opener will ensure maximal gap junction communication between the different cells considered to play an important role in the complicated repair process and thereby improve the wound repair. The compound will be administered topically, systemically or orally.

E. Diabetic Retinopathy

Diabetic retinopathy can be diagnosed very early after onset of the disease by identifying alterations in the rate of blood flow (Bursell S-V, et al. (*Curr Eye Res*. 1992; 11: 287–95), breakdown in the blood-retinal barrier (Cunha-Vaz J G, et al. (*Br J Ophthalmol*. 1975; 59: 649–56), Do Carmo A, et al. (*Exp Eye Res*. 1998; 67: 569–75)) and/or loss of autoregulation (Kohner E M, Patel V, Rassam S M B. (*Diabetes* 1995; 44: 603–607)). By using both tracer transport and double cell patch clamp techniques Oku H, et al. (*Invest Ophthalmol Vis Sci*. 2001; 42: 1915–1920) have demonstrated an extensive cell-to-cell coupling. A closure of gap junction pathways disrupts the multicellular organization of retinal microvessels and contribute to diabetic retinal vascular dysfunction. Zhou Z Y, et al. (*Neuroscience*. 2001; 102: 959–67) further demonstrated that reactive oxygen are involved in retinal gap junctional uncoupling and a recoupling when gluthation is supplied.

Hemichannel closers' effect on diabetic retinopathy can be studied in vitro using the streptozotocin induced diabetic rat model as described above. Freshly isolated retinal microvessels (Sakagami K, et al. *J Physiol* (*Lond*). 1999; 521: 637–50) will be transferred to coverslip as described by Oku H, et al. (*Invest Ophthalmol Vis Sci*. 2001; 42: 1915–1920). In this preparation the intercellular communication between the cells in the vascular wall will be measured either with dye or with tracer. Different concentrations in the range of 10–10–10–7 M of the compounds of the invention, eg., gap junction openers compound 1 or compound 2 can be tested and a significant increase in intercellular communication compared to baseline will be seen in the diabetic retina. Similar improvement will be seen when compared to controls (healthy animals). Treatment will be systemic, locally or orally. Therapy is preferably an add-on to conventional antidiabetic treatment.

Not only diabetic retinopathy but also other vascular abnormalities in the retina as for instance arteriosclerosis will benefit from increased closing of hemichannels or an improved gap junction communication by treatment with a compound that assist Cx tyrosine phosphorylation compound will be administered parenterally.

F. Cardiac Disorders

1. Atrial-ventricular (AV) Blockade

Intercellular communication in the cardiac av node is maintained via gap junctions. Decreased function lead to decreased conduction and may lead to total a-v blockade.

AV blockade is seen in acute myocardial infarction, in ischaemic heart disease, digitalis intoxication, calcium channel blocker intoxication and a hemichannel closing compound will improve the av conduction. Administration of hemichannel closing compound shall be either parenterally or orally.

2. Atrial Fibrillation

Nao et al. 2001 have found decreased serine phosphorylation of connexin 40 in myocardial cells of patients suffering from chronic atrial fibrillation (AF). Decreased serine phosphorylation of connexin is known to be connected with uncoupling of cells which may lead to AF. If this condition of chronic AF is also characterized in decreased tyrosine phosphorylation of connexins, then treatment with a compound such as Compound 1 or 2 herein may increase tyrosine phosphorylation, close hemichannels, open gap junction channels and remove the causes of AF.

3. Ischemia/Reperfusion Injury

During regional ischemia, hearts are exposed to metabolic stress that causes cell swelling which in turn increases tissue pressure and reduces perfusion of the ischemic border zone tissue. It is believed that the reduced perfusion in the ischemic border zone contributes to the gradual spreading of the infarct, which is associated with further impairment of cardiac function. As shown in Examples 7 and 8, Compound 1 prevents cell swelling during ischemia, reduces infarct size and prevents impairment of cardiac function after myocardial infarction.

Moreover, coronary perfusion is restablished in patients with myocardial infarction by either administering a thrombolytic agent or by percutaneous transluminal coronary angioplasty (PTCA). Although restoration of blood flow is a prerequisite for myocardial salvage, reperfusion itself may lead to additional tissue injury beyond that generated by ischemia alone—this is known as "reperfusion injury". Mechanisms proposed to contribute to reperfusion injury are many, including oxygen free radical overload, neutrophil-mediated myocardial injury, intracellular calcium overload, and changes in osmotic environment (Wang et al., *Cardiovasc Res*. 2002 July; 55(1):25–37. Review).

Figure 9A:
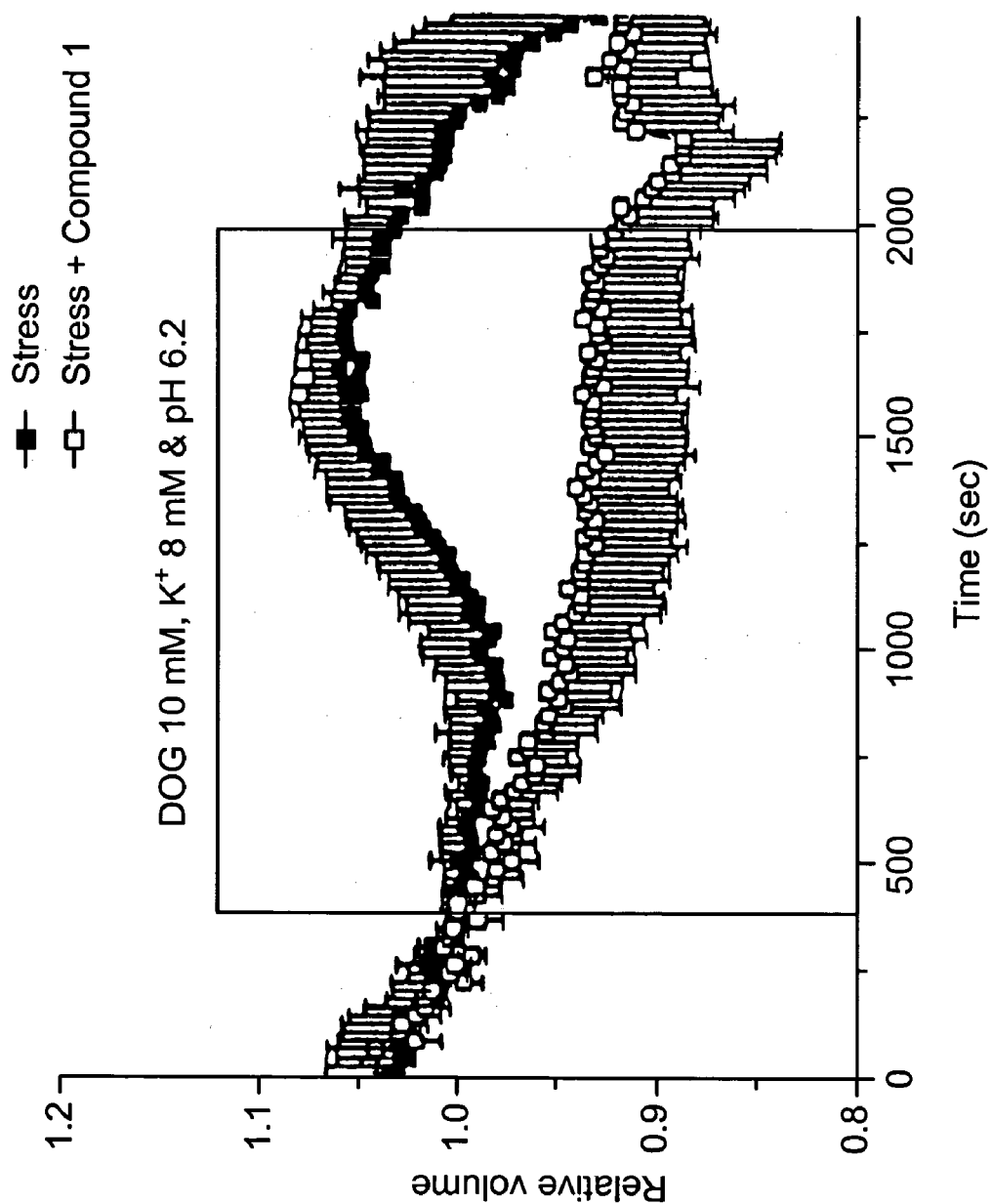
FIG. 9A–B are graphs showing effect of compound 1 on stress-induced cell swelling.

There is recognition that the osmolarity of bodily fluids is strictly controlled so that most cells do not experience changes in osmotic pressure under normal conditions, but osmotic changes can occur in pathological states such as ischemia, septic shock, and diabetic coma. The primary effect of a change in osmolarity is to acutely alter cell volume. If the osmolarity around a cell is decreased, the cell swells, and if increased, it shrinks. In order to tolerate changes in osmolarity, cells have evolved volume regulatory mechanisms activated by osmotic challenge to normalise cell volume and maintain normal function. In the heart, osmotic stress is encountered during a period of myocardial ischemia when metabolites such as lactate accumulate intracellularly and to a certain degree extracellularly, and cause cell swelling. This swelling may be exacerbated further on reperfusion when the hyperosmotic extracellular milieu is replaced by normosmotic blood and it may even cause rupture of the cardiac cell membranes (Wright A R, Rees S A.: *Pharmacol Ther*. 1998 October; 80(1):89–121. Review). Thus, it is believed that compounds selected in accord with the present invention will prevent myocardial damage during reperfusion, eg., by a mechanism similar to the effect described in Example 7 (FIG. 9A).

In addition, it has been reported that during the commonly used PTCA procedure, the atheroschlerotic plaque is ruptured which causes microembolization in the microcirculation distal to the site of the PTCA procedure, which is associated with accelerated progression of heart failure and increased mortality Henriques J P et al: *Eur Heart J* 2002 July; 23(14):1112–7). As shown in Examples 7 and 8, Compound 1 prevents cell swelling during ischemia, reduces infarct size and prevents impairment of cardiac function after mypocardial infarction and these properties of compounds will reduce injury during reperfusion.

Accordingly, the invention provides a method of cytoprotecting tissue or an organ of a mammal in need of such treatment. In one embodiment, the method includes administering a therapuetically effective amount of at least one compound selected from the group consisting of the compounds represented by Formula I or II. By the phrase "cytoprotecting" is meant reducing, preventing or alleviating symptoms associated with unwanted cell swelling. Particular tissues and organs that will benefit from the method include those confined or otherwise impacted by a fiborous capsule such as heart or kidney. Also included are tissues associated with bone such as brain, spinal cord and bone marrow.

In one embodiment, the method further includes exposing the tissue or organ of the mammal to ischemic conditions such as those described herein. An example is heart infarction (heart attack) in which the ischemia is associated with harmful myocardial cell swelling. In one embodiment, such swelling can be reduced or avoided by administering at least one of Ac-D-Tyr-D-Pro-D-4Hyp-Gly-D-Ala-Gly-NH2 (Compound 1) and Ac-Gly-Asn-Tyr-NH2 (Compound 2) to the mammal.

As discussed a method of preventing or treating reperfusion injury in a mammal is also provided by the invention. In one embodiment, the method includes administering a therapuetically effective amount of at least one compound selected from the group consisting of the compounds represented by Formula I or II. In a more specific embodiment, the method further includes the heart of the mammal to infarct conditions. According to the method, it is desirable to establish coronary perfusion, typically as quickly as possible. In some embodiments, the method will further include administering a thrombolytic agent (eg., tissue plasminogen activator ("TPA")) or providing coronary angioplasty to facilitate coronary perfusion into the infarcted heart. In one embodiment, the compound is at least one of Ac-D-Tyr-D-Pro-D-4Hyp-Gly-D-Ala-Gly-NH2 (Compound 1) and Ac-Gly-Asn-Tyr-NH2 (Compound 2).

G. Immunology: Cell Maturation

Cell-to-cell interactions are crucial for lymphocyte maturation and activation. A wide rage of membrane molecules ensure intercellular adhesion and enabling cell-cell signalling during cell migration and activation in the immune system. Circulating human T, B and NK lymphocytes express Cx43 and active gap junctions between the cells have been demonstrated using dye methods as described previously. It has also been demonstrated that decrease in intercellular gap junctional coupling markedly decrease the secretion of IgM, IgG and IgA indicating that intercellular signaling across gap junctions is an important component of the mechanisms underlying metabolic cooperation in the immune system (Oviedo-Orta E, et al. (*Immunology*. 2000; 99: 578–90), Oviedo-Orta E, et al. (*FASEB*. 2001; 15:768–774)).

In subchronic or chronic inflammation a local increase in synthesis of immunglobulins is desirable independent of aethiology. During inflammation the tissue is often different from the normal healthy tissue and low oxygen tension produces uncoupling of the intercellular gap junctional communication. The importance of low oxygen for GJIC uncoupling has been demonstrated in several different cell systems suggesting that oxygen tension is a universal regulator of GJIC. Said uncoupling is a result of altered tyrosine and/or serine and/or threonine phosphorylation of connexins in gap junction channels, and administration of a compound of the invention such as compound 1 or 2 herein will counteract this effect, close hemichannels and restore GJIC.

H. Improving GJIC

There are basically two ways of maintaining GJIC, either by keeping gap junction channels open or by facilitation of docking of hemichannels. In the treatment or prevention of disease states characterized in presence of ischemic conditions, both ways are preferred or recommended.

In primary cultures of neonatal rat ventricular cardiomyocytes, deprivation of oxygen and glucose leads to a decrease in the noradrenalin-induced stimulation of phosphoinositol (PI) turnover to app. 50% of the level at normal atmospheric and nutritional conditions. The gap junction modifier compound 1 has been shown to normalise this impaired noradrenalin-induced stimulation of PI turnover during oxygen and glucose deprivation by raising PI turnover to app. 90% of the normal level. Moreover is has been shown that compound 1 does not alter the noradrenalin-induced level of PI turnover during normal atmospheric and nutritional conditions (Meier, E and Beck, M M: 2001 International Gap Junction Conference, Aug. 4–9, 2001, Hawaii, USA, abstract no. 132). Likewise, in cultured human osteoblast cultures and in osteoblastic rat osteosarcoma cell lines hypoxia decreased intracellular calcium wave propagation as measured as dye transfer after Lucifer Yellow injections. This decrease could be completely reversed by treatment with compound 1 (Teilmann, S C, et al.: 2001 International Gap Junction Conference, Aug. 4–9, 2001, Hawaii, USA, abstract no. 176).

Due to cellular uncoupling during inflammation, for instance, a compound that closes hemichannels and opens gap junctions will improve synthesis of immunglobulins during inflammation.

I. Peripheral Neuropathy and Neuropathic Pain

Peripheral neuropathy and pain as seen in diabetes, during dialysis, liver cirrhosis and many other conditions are reported to involve both somatic and autonomic nerves. The exact mechanisms of the peripheral nerve injury in the various conditions are under investigation but nerve terminal destruction, decreased conductance, demyelination and increased inflammatory response have been described. Common for the various conditions in experimental set up are that increased free radicals, increased nitric oxide, oxygen stress and lack of free radical scavengers are seen and reduction of gap junction communication is recorded (Pitre D A, et al. (*Neurosci Lett*. 2001; 303: 67–71), Bolanos J P, Medina J M. (*J Neurochem*. 1996; 66: 2019–9), Low P A, Nickander, K K. (*Diabetes*. 1991; 40: 873–7), Levy D, et al. (*Neurosci Lett*. 1999; 260: 207–9), Bruzzone R, Ressot C. *J Eur Neurosci*. 1997; 9: 1–6)). Thus, a compound of the invention that assists hemichannel closing by phosphorylating hemichannel connexins will be beneficial in the treatment of peripheral neuropathy. Administration will be parenterally.

J. Hearing Deficit

Noise induced hearing loss, presbycusis known to be associated with production of free radicals are related to inhibition of gap junction coupling between both Hensen cells and Deiters cells from Corti's organ in the cochlea (Todt I, et al. (*J Membrane Biol*. 2001; 181: 107–114), Blasits S, et al. (*Phlugers Arch*. 2000; 440: 710–12) Lagostena L, et al. (*J Physiol*. 2001; 531: 693–707)). The gap junction communication between these supporting cochlear cells provides the important homeostasis for the sensory cells and thereby a normal neuronal activity of outer hair cells (Johnstone B M, et al. (*J Physiol* 1989; 408: 77–92)). This communication is disrupted during oxidative stress (Todt I, et al. (*J Membrane Biol*. 2001; 181: 107–114). Acquired or age dependent hearing loss will be prevented when treated with a compound which can increase phosphorylation of tyrosine residues in connexin hemichannels (close the hemichannels) and maintain gap junction communication in the supportive cells. A suitable compound of the invention can be administered parenterally.

Melanocytes in the vestibular organ dark cell area are communicating heavily via gap junction and may play a role in transporting material between the endolymph and perilymph and also be of importance in maintaining the homeostasis of the microenvironment in the inner ear (Masuda M, et al. (*Anat Rec*. 2001; 262; 137–146)). Endolymphatic hydrops is related to various clinical conditions characterized by dizziness and reduced hearing. A decreased capacity of gap junction communication may be of importance in regulating transmembrane transport of several substances originally secreted or excreted via specific types of transporters.

K. Age Dependent Anemia and Bone Marrow Transplantation

Existence of functional gap junctions between haematopoietic progenitor cells and stromal cells of the haematopoietic microenvironment was many years controversial but studies have now proofed the existence of human gap junction communication (Rosendaal M, et al. *Tissue Cell*. 1991; 23: 457–470), Dürig J, et al. (*Brit J Haematol*. 2000; 111: 416–25)). It has also been demonstrated that the communication is bi-directional favoring the hypothesis that stromal cells control the proliferative behaviour of the haematopoietic progenitor cells, but also their functional status can be regulated by immature haematopoietic cells (Gupta P, et al. (*Blood*. 1998; 91: 3724–3733)).

With age the functionality of the haematopoietic tissue is decreased and anemia is often seen in elderly people. Reduced capacity of haematopoietic tissue is also seen in haematological malignancies and after treatment with chemotherapeutics. Bone marrow transplantation from donor is used to prevent pancytopenia.

The effect of a compound of the invention that assists in hemichannel closing and/or facilitates gap junction communication will be studied in pretreated rats exposed to high dose cyclophosphamide. In these animals the bone marrow has stopped producing mature haematopoietic cells. Number of reticulocytes at different time intervals after cyclophosphamide will be significantly higher in the animals pretreated with the connexin tyrosine phosphorylating compound 1 using doses of about 100 µL of $10^{-10}$ M to about $10^{-8}$ M compound 1 compared to non-pretreated animals. Administration of suitable compounds of the invention will be parenterally.

L. Pituitary and Hypothalamic Hypofunction

Hormones from the anterior pituitary gland show circadian variation in secretion within minutes, hours, days and seasons. The part of the nervous system responsible for most circadian rhythm is localized to a pair of structures in the hypothalamus known as the suprachiasmatic nucleus. In this center this biological clock is intrinsic in the individual cells. However coordinated electrical activity is mediated to neighboring cells via gap junction communication. (Colwell C S. (*J Neurobiol*. 2000; 43: 379–88)). Because also the anterior pituitary lacks direct innervations, gap junction-mediated cell-to-cell communication within the gland must be indispensable for the adequate cell-to-cell coordination and synchronization required to ensure appropriate and timed hormone secretion. (Vitale M L, et al. (*Biol Reporo*. 2001; 64: 625–633)). Guerineau N C, et al. (*J Biol Chem*. 1998; 273: 10389–95) concluded that spontaneously active endocrine cells are either single units or arranged in synchronized gap junction-coupled assemblies scattered throughout the anterior pituitary gland. Synchrony between spontaneously excitable cells may help shape the patterns of basal secretion. From the anterior pituitary gland, growth hormone, prolactin, adrenocortical hormone, thyroid hormone, and gonadotropin hormones are synthesized under control from hypothalamus stimulating hormones. One of the mechanism in dysrhythm of the complicated hypothalamic-pituitary-endocrine glands within one of the axis is therefore also related to reduced communication via gap junctions. The diseases are diabetes insipidus, hypogonadotrope hypogonadism, myxoedema, adrenocorticoid hypofunction, and dwarfism. Treatment with a suitable compound of the invention, preferably a gap junction opener, can improve the symptoms.

Also the neurons in the suprachiasmatic nucleus of the hypothalamus are dependent on optimal gap junction communication. In the axis mentioned above gap junction opener with mode of action in this region will also benefit patients with disturbed circadian rhythm (Shinohara K, et al. (*Neusosci Lett*. 2000; 286: 107–10).

M. Renovascular Hypertension and Nephrotoxicity

Kidney and endothelial specific gap junctions are widely distributed in the kidney found in glomeruli, tubulus and vasculature including intraglomerular capillaries and juxaglomerular arterioles (Haefliger J-A, et al. (*Kidney Int*. 2001; 60: 190–201)). In that study the authors demonstrated the presence of gap junctions connecting renin-secreting cells of the afferent arteriole. The role of gap junction might contribute to the detection and propagation of blood borne signals, such as those elicited by increased blood pressure. Within the kidney, such signals need to be converted into autocrine, paracrine and endocrine stimuli by the endothelial cells of the afferent arteriole and the transmitted to the renin-secreting cells. Gap junction communication plays thus an important role in forming the interconnected juxtaglomerular apparatus. The rapid open to close transitions of gap junctions channels further imply a readily response to local vascular changes ensuring the continuous feedback required to match glomerular and tubular function as well as renin secretion to physiological demands. Diseases characterized by impaired renal gap junction communication will benefit from treatment with compound of the invention, preferably a specific gap junction opener, either administered orally or parenterally.

Heavy metals are nephrotoxic and causes renal injury. It has been demonstrated that the toxic metals cadmium (Fukumoto M, et al. (*Life Sciences*. 2001; 69:247–54)) as well as mercury (Yoshida M, et al. (*Arch Toxicol*. 1998; 72: 192–96)) in primary cell cultures from rat proximal tubulus uncouple gap junctions and both groups suggest that renal dysfunction is related to the reduced intercellular communication. Treatment of heavy metal poisoning with a connexin tyrosine phosphorylating compound will reduce the tissue damage and prevent the progressive tissue devastation.

An in vitro test can be performed in cell cultures from tubulus cells and the compounds (compound 1 or compound 2 in a concentration of about $10^{-10}$–$10^{-7}$ M) prevention of gap junction uncoupling when exposed to heavy metals will be investigated. Gap junction communication will be tested with Lucifer dye method as described previously.

After systemic administration of heavy metal to experimental animals (rats) renal function will be measured using $^3$H-insulin as a clearance marker for glomerular filtration rate, $^{14}$C-labelled tetraethylammonium as a clearance marker for renal plasma flow and lithium as a marker for proximal tubular function (Petersen J S, et al. *J. Pharmacol. Esp. Ther*. 1991, 258:1–7) before and after different time of chronic treatment with heavy metals. Chronic treatment with a specific compound of the invention, such as compound 1, will be initiated when renal function is compromised and an significant improvement of renal function parameters (glomerular filtration rate and blood pressure) will be seen following the treatment. Administration of a suitable invention compound will be parenterally.

Non-infectious inflammation as well as infections with different microbes induces significant non specific chronic changes in renal function also characterized by reduced glomerular filtration rate, decreased excretion of electrolytes and water and changes in blood pressure. Some of these symptoms will as well be treated with a specific connexin tyrosine phosphorylating compound and the symptoms will decline.

N. Developing and Remodelling of Teeth

Murakami S and Muramatsu T (Anat Embryol. 2001; 203: 367–374) confirmed previous studies that gap junction communication exists between odontoblasts and that cellular activity is coordinated via these intercellular bridges (Iguchi Y, et al. (*Arch Oral Biol*. 1984; 29: 489–497)) but in their recent study they also demonstrated that these gap junction communications are present during the early development of teeth (pre-odontoblast) as well as in the odontoblasts in young and old odontoblast. Also the pulp cells subjacent to odotoblasts have gap junctions. These findings indicate that intercellular gap junction communication is important both during development of the teeth and during lifetime when teeth are remodeled or wormed.

Treatment with a connexin phosphorylating compound of the invention, such as compound 2 which can be tested in vitro for effect on odontoblast intercellular communication in an assay which is essentially comparable to the osteoblast assays described herein, will normalize disturbed development of teeth. Treatment will also facilitate remodeling of teeth and make the teeth more resistant to caries.

O. Stem Cells

Lumelsky et al (2001) have generated cells expressing insulin and other pancreatic endocrine hormones from mouse embryonic stem cells. See Nadya Lumelsky et al. in *Differentiation of Embryonic Stem Cells to Insulin-Secreting Structures Similar to Pancreatic Islets. Science*, 292, 1389–1394, 2001). The cells self-assemble to form three-dimensional clusters similar in topology to normal pancreatic islets where pancreatic cell types are in close association with neurons. Glucose triggers insulin release from these cell clusters by mechanisms similar to those employed in vivo. When injected into diabetic mice, the insulin-producing cells undergo rapid vascularization and maintain a clustered, islet-like organization.

In the clinical context, this embryonic stem cell-based system will allow simultaneous generation and assembly of insulin-secreting and other islet cell types known to play important role in regulation of insulin secretion into functional structural units. These units can provide material to optimize insulin production and analyze the fine control of glucose homeostasis embryonic stem cells are ideal for these studies because genetic tools can be used to define the molecular basis of islet development and function. Potential for cell-based therapies is clearly an attractive goal for applications involving human and nonhuman embryonic stem and embryonic germ cells. Adult tissue may also be a useful source of functional pancreatic cells. The differentiation system described here may provide a source of functional pancreatic islets for treatment of diabetes. This is the first report showing that the several cell types of endocrine pancreas can be generated from embryonic stem cells in vitro. Although pancreatic islets obtained from cadavers can function in the liver after grafting, issues of tissue rejection and availability remain to be resolved. It is clear that engineering of embryonic stem cells to produce an abundant source of immunocompatible tissue for transplantation holds a growing promise for surmounting this and other problems associated with diabetes.

Myocardial infarction leads to loss of tissue and impairment of cardiac performance. The remaining myocytes are unable to reconstitute the necrotic tissue, and the post-infarcted heart deteriorates with time. Injury to a target organ is sensed by distant stem cells, which migrate to the site of damage and undergo alternate stem cell differentiation; these events promote structural and functional repair. This high degree of stem cell plasticity prompted Orlic et al (*Nature* 410, 701–705 (2001)) to test whether dead myocardium could be restored by transplanting bone marrow cells in infarcted mice. They sorted lineage-negative (Lin–) bone marrow cells from transgenic mice expressing enhanced green fluorescent protein by fluorescence-activated cell sorting on the basis of c-kit expression. Shortly after coronary ligation, Lin– c-kitPOS cells were injected in the contracting wall bordering the infarct. They found that newly formed myocardium occupied 68% of the infarcted portion of the ventricle 9 days after transplanting the bone marrow cells. The developing tissue comprised proliferating myocytes and vascular structures. Their studies indicate that locally delivered bone marrow cells can generate de novo myocardium, ameliorating the outcome of coronary artery disease.

To characterize further the properties of these myocytes, they determined the expression of connexin 43. This protein is responsible for intercellular connections and electrical coupling through the generation of plasma-membrane channels between myocytes; connexin 43 was apparent in the cell cytoplasm and at the surface of closely aligned differentiating cells. These results were consistent with the expected functional competence of the heart muscle phenotype.

Since functional cells are generated from embryonic stem cells, and since connexins are indeed expressed in these cells in infarcted heart tissue, it is believed that this will be the case for other cells differentiated from embryonic stem cells. Since connexins play a dominating role in the function of these tissues (including pancreatic beta cells and heart muscle cells). compounds of the invention such as compound 1 and compound 2 that increase connexin tyrosine phosphorylation and hemichannel closing (resulting also in increased gap junction communication) will enhance the proliferation of embryonic stem cells into functional cells in organs wherein stem cells have been implanted.

Thus it is an object of the invention to provide connexin tyrosine phosphorylating compounds such as compound 1 and compound 2 to stimulate the transition of stem cells to functional cells in transplanted organs like pancreas for treatment of diabetes mellitus, heart for treatment of heart infarction, and basal ganglia of the brain for treatment of Parkinsons disease. In general, it is believed that these compounds will accelerate diffentiation of stem cells, which may accelerate healing processes in all organs such as heart, brain, skin, bone, pancreas, liver, and other internal organs. Experiments can be performed using the general experimental design with myocardial infarction as described above by Orlic et al, supra, with administration of compound 1 and compound 2, for instance, repeatedly during the proliferation process. These experiments are believed to show an increase in connexin 43 expression by compound 1 and compound 2 or a faster regenerative process.

P. Cancer

1. Tumor Progression

During tumorigenesis, the interruption of the physiological interaction of normal cells with their neighboring cells, and loss of features of differentiation are a common denominator in tumor progression. Alteration in gap junction communication is believed to be among the earliest changes during cell tumorgenesis (Wolburg H, Rohlmann A. *Int Rev Cytol.* 1995; 157: 315–73), Klaunig J E, Ruch R J. 1990; 135–46)).

Kyung-Sun Kang, et al. (*Cancer Letters* 166 (2001) 147–153) have shown that pre- and co-incubation with GeO2 in TPA treated rat liver epithelial cells abolished down-regulation of GJIC by TPA suggesting that a substance that recovers the inhibition of GJIC may be used in the prevention or inhibition of tumor promotion. Suzuki J, Na H-K, et al. (*Nutrition and Cancer*, vol 36 No. 1 p. 122–8) have shown that the food additive lambda-carrageenan inhibits GJIC in rat liver epithelial cells similar to that of the well-documented tumor promotor phorbol ester (TPA), and therefore could play a role in carcinogenesis as a tumor promoting agent. Thus, the compounds of the present invention may be used in the prevention or treatment of cancer caused by tumor promoting agents, such as TPA and lambda-carrageenan.

2. Drug Sensitivity Resistance

Increased gap junction communication improves the microenvironment in tumors. See Chen et al.: Chem Biol Interact 1998 Apr. 24; 111–112:263–75

3. Metastasis

Loss of intercellular gap junction communication is associated with high metastatic potential in all cancers with metastatic potentials. (Saunders M M, et al. *Cancer Res.* 2001; 61: 1765–1767), Nicolson G I, et al. *Proc. Natl Acad Sci USA*. 1988; 85: 473–6)). Prevention of metastasis is established by treatment with a connexin tyrosine phosphorylating compound which will assist in preserving the gap junction communication in tumors. Treatment is an add on to conventional chemotherapy.

It is believed that administration of one or a combination of the invention compounds in a therapeutically effective amount (eg., compound 1 or compound 2) will be able to prevent or treat cancer.

Q. Miscellaneous Cells

Gap junctions also play an important role in intercellular communication, proliferation and differentiation in gastric mucosal cell. Gap junction opener will stimulate regenerative processes after induced injury (Endo K, et al. (*J Gastroenterol Hepatol*. 1995; 10: 589–94)).

The cytoarchitecture of meniscal cells partly depends on gap junction communication. The fibrocartilage part of the meniscal as well as the fibrocartilage structure of tendons depends on intercellular communication. During injuries gap junction openers will improve the speed of repair.

R. Epilepsy

It may be desirable to treat disease states such as epilepsia characterized in abnormally high GJIC with a hemichannel opener, preferably as an adjuvant therapy in order to allow uptake of drugs or small regulatory molecules that serve to uncouple gap junction channels.

It is an object of the present invention to provide methods to treat or prevent one or more of the medical indications or conditions described herein. Typically, but not exclusively, such methods will include administration of at least one of the foregoing compounds, preferably one of same, in an amount sufficient to treat, prevent, or reduce the severity of the indication or condition. Preferred compounds have been selected by one or a combination of the in vitro and in vivo assays described herein. Particular administration strategies will be apparent of those of skill in this field and will vary depending eg., on the sex, weight, general health and specific indication or condition to be treated or prevented. As discussed, the compounds disclosed herein can be employed as the sole active agent in invention methods. Alternatively, they can be used in "add-on" therapies such as those in which use of the compounds in conjunction with a recognized treatment method is indicated. Preferred indications or conditions to be treated or prevented in accord with the invention are generally associated with impaired cellular communication or impaired gap junction function. More specific indications and conditions relating to the invention have been discussed above.

Treatment methods in accord with the invention can employ one or more of the compounds disclosed herein as the sole active agent. Preferably, one of the compounds will be employed. If desired, such compounds can be used prophylactically ie., to prevent or reduce the severity of a particular indication or condition. Alternatively, the compounds can be used in conjunction with a recognized therapeutic approach. As an illustration in embodiments in which irradiation is treated, it is generally preferred that the treatment method be "add on" ie., in conjunction with a recognized therapy for treating the condition. Such "add on" treatment methods of the invention can be conducted at the same time or at a different time then the recognized therapy as needed. Established therapeutic approaches for a variety of diseases and medical conditions have been described. See generally, *Harrison's Principles of Internal Medicine* (1991) 12 ed., McGraw-Hill, Inc. and *The Pharmacological Basis of Therapeutics* (1996) Goodman, Louis S. 9th ed Pergammon Press, for example; the disclosures of which are incorporated herein by reference.

The concentration of one or more treatment compounds in a therapeutic composition will vary depending upon a number of factors, including the dosage of the hemichannel modulating compound to be administered, the chemical characteristics (e.g., hydrophobicity) of the composition employed, and the intended mode and route of administration. In general terms, one or more than one of the hemichannel modulating compounds may be provided in an aqueous physiological buffer solution containing about 0.1 to 10% w/v of a compound for parenteral administration.

It will be appreciated that the actual preferred amounts of active compounds used in a given therapy will vary according to e.g. the specific compound being utilized, the particular composition formulated, the mode of administration and characteristics of the subject, e.g. the species, sex, weight, general health and age of the subject. Optimal administration rates for a given protocol of administration can be readily ascertained by those skilled in the art using conventional dosage determination tests conducted with regard to the foregoing guidelines. Suitable dose ranges may include from about 1 µg/kg to about 100 mg/kg of body weight per day ("therapeutically effective amount").

Therapeutic compounds of the invention are suitably administered in a protonated and water-soluble form, e.g., as a pharmaceutically acceptable salt, typically an acid addition salt such as an inorganic acid addition salt, e.g., a hydrochloride, sulfate, or phosphate salt, or as an organic acid addition salt such as an acetate, maleate, fumarate, tartrate, or citrate salt. Pharmaceutically acceptable salts of therapeutic compounds of the invention also can include metal salts, particularly alkali metal salts such as a sodium salt or potassium salt; alkaline earth metal salts such as a magnesium or calcium salt; ammonium salts such an ammonium or tetramethyl ammonium salt; or an amino acid addition salts such as a lysine, glycine, or phenylalanine salt. Additionally suitable salts are provided below.

More particular hemichannel modulating compounds of the invention are used in the form of a pharmaceutically acceptable salt, an alkyl ester, an amide, an alkylamide, a dialkylamide or a hydrazide formed with the C-terminal carboxylic acid function of a linear compound or a free carboxylic acid function, if present, of a cyclic compound. Amides and lower alkyl amides of linear compounds are among the preferred compounds of the invention. Salts include pharmaceutically acceptable salts, such as acid addition salts and basic salts. Examples of acid addition salts have already been described and include hydrochloride salts, sodium salts, calcium salts, potassium salts, etc. Examples of basic salts are salts where the cation is selected from alkali metals, such as sodium and potassium, alkaline earth metals, such as calcium, and ammonium ions $^+N(R^3)_3(R^4)$, where $R^3$ and $R^4$ independently designate optionally substituted $C_{1-6}$-alkyl, optionally substituted $C_{2-6}$-alkenyl, optionally substituted aryl, or optionally substituted heteroaryl. Other examples of pharmaceutically acceptable salts are; e.g., those described in *Remington's Pharmaceutical Sciences* 17. Ed. Alfonso R. Gennaro (Ed.), Mark Publishing Company, Easton, Pa., U.S.A., 1985 and more recent editions, and in *Encyclopedia of Pharmaceutical Technology*.

In the therapeutic methods of the invention, a treatment compound can be administered to a subject in any of several ways. For example, a hemichannel modulating compound selected in one or a combination of the in vitro and/or in vivo assays provided can be administered as a prophylactic to prevent the onset of or reduce the severity of a targeted condition. Alternatively, the compound can be administered during the course of a targeted condition.

A treatment compound can be administered to a subject, either alone or in combination with one or more therapeutic agents, as a pharmaceutical composition in mixture with conventional excipient, i.e. pharmaceutically acceptable organic or inorganic carrier substances suitable for parenteral, enteral or intranasal application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Such compositions may be prepared for use in parenteral administration, particularly in the form of liquid solutions or suspensions; for oral administration, particularly in the form of tablets or capsules; intranasally, particularly in the form of powders, nasal drops, or aerosols; vaginally; topically e.g. in the form of a cream; rectally e.g. as a suppository; etc.

The pharmaceutical agents may be conveniently administered in unit dosage form and may be prepared by any of the methods well known in the pharmaceutical arts, e.g., as described in *Remington's Pharmaceutical Sciences* (Mack Pub. Co., Easton, Pa., 1980). Formulations for parenteral administration may contain as common excipients such as sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of certain hemichannel modulating compounds of the invention.

Other potentially useful parenteral delivery systems include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or citric acid for vaginal administration. Other delivery systems will administer the therapeutic agent(s) directly at a surgical site, e.g. after balloon angioplasty a hemichannel modulating compound may be administered by use of stents.

Abbreviations and Formulae:

Throughout the description and claims the three letter code for natural amino acids is used as well as generally accepted three letter codes for other α-amino acids, such as Sarcosin (Sar), α-Amino-iso-butanoic acid (Aib), Naphthylalanine (Nal) including 1-naphthylalanine (1Nal) and 2-naphthylalanine (2Nal), Phenylglycine Phg, 2,4-Diaminobutanoic acid (Dab), 2,3-Diaminopropanoic acid (Dapa), and Hydroxyproline (Hyp). Where nothing is specified Hyp represents 4-hydroxyproline. The natural or essential amino acids are the amino acid constituents of proteins. The aromatic amino acids are Phe, Tyr, Trp, 1Nal, 2Nal and His. Where the L or D form has not been specified it is to be understood that the amino acid in question has the natural L form, cf. *Pure & Appl. Chem*. Vol. 56(5) pp 595–624 (1984). Where nothing is specified it is to be understood that the C-terminal amino acid of a compound of the invention exists as the free carboxylic acid, this may also be specified as "—OH". The C-terminal amino acid of a compound of the invention may be shown to have the terminal function "—OH/NH$_2$," which means that there are two preferred forms of the compound: the free carboxylic acid and the amidated derivative.

The following specific definitions apply unless otherwise specified: ASAL refers to 4-azidosalicyloyl radical; AB refers to 4-azidobenzoyl radical; Fmoc refers to 9-fluorenylmethyloxycarbonyl radical; Ac refers to acetyl radical. Throughout the present disclosure unless otherwise specified the following definitions apply; Acm refers to acetamidomethyl radical; T4c refers to L-thiazolidin-4-carboxylic acid radical; Pc refers to L-pipecolic acid radical; DNP refers to dinitrophenyl; DBF is defined as 2-aminoethyl-6-dibenzofuranpropionic acid; Acm refers to acetamidomethyl; and Sar refers to sarcosinyl radical; DNP functions is a hapten for antibody recognition, and compounds of the invention that contain a DNP moiety may be preferably used as research tools.

See also PCT/DK01/00127 (WO 01/62775) and PCT/US02/05773 (WO 02/077017) for additional information.

All references disclosed herein are incorporated by reference. The following Examples are illustrative of the invention.

REFERENCE EXAMPLE 1

Standard In Vivo Mouse Arrythmia Assay

It is possible to test for antiarrythmic effects by performing a calcium-induced arhythmia model in mice.

Briefly, the antiarrhythmic effects of compounds can be tested in an in vivo model of calcium-induced arrythmias according to the model of J. J. Lynch, R. G. et al. *J Cardiovasc. Pharmacol.* 1981, 3 49–60. Mice (25–30 g) were anaesthetised with a neurolept anaesthetic combination (Hypnorm® (fentanyl citrate 0.315 mg/ml and fuanisone 10 mg/ml)+midazolam (5 mg/ml)). Commercial solutions of hypnorm and midazolam were diluted 1:1 in distilled water and one part diluted Hypnorm® is mixed with one part diluted midazolam.

The anaesthesia was induced by s.c. administration in a dose of 0.05–0.075 µl/10 gram mouse. An i.v. cannula was inserted into the tail vein. The lead II ECG signal was recorded continuously by positioning of a stainless steel ECG electrodes on the right forelimb and on the left hind limb. The ground electrode was placed on the right hind limb. The signal was amplified (×5.000–10.000) and filtered (0.1–150 Hz) via a Hugo Sachs Electronic model 689 ECG module. The analogue signal was digitised via a 12 bit data acquisition board (Data Translation model DT321) and sampled at 1000 Hz using the Notocord HEM 3.1 software for Windows NT. After a 10-min equilibration period, the test sample of drug was injected into the tail vein. Mice pretreated with vehicle were tested as a measure of the control level in untreated animals. The injection volume was 100 µl in all experiments. Infusion of CaCl$_2$ (30 mg/ml, 0.1 ml/min≈100 mg/kg/min (calciumchlorid-2-hydrat, Riedel-de Haën, Germany)) was started 3 min after i.v. administration of drug or vehicle. The time lag to onset of 2nd degree AV-block was determined as the time from the start of CaCl$_2$ infusion until the first arrhythmic event occured. An event of 2nd degree AV-block was defined as intermittent failure of the AV conduction characterised by a P-wave without the concomitant QRS complex.

Responses were expressed relative to the time until 2nd degree AV-block occurred in vehicle treated mice. Maximal effect of each of the tested substances has been summarized.

More particular methods for detecting candidate compounds with good gap junction modifying activity further include selecting candidate compounds that prolong the time until onset of the induced atrial ventricular (AV) block by at least about 20% (score at least 2) in the standard in vivo mouse arrhythmia assay. More preferred compounds exhibit a prolongation of at least about 60% of the time until onset of the induced AV block (score at least 3) in the assay.

The following examples provide a functional assay that shows the ability of compound 1 to both open gap junction channels and close hemichannels in rat neonate cardiomyocytes. Thus, it is possible to obtain differentiated regulation of GJIC by tyrosine phosphorylation of both hemichannels and gap junction channels.

EXAMPLE 1

Antiarrhythmic Compounds compounds used in the invention include Ac-D-Tyr-D-Pro-D-4Hyp-Gly-D-Ala-Gly-NH2 (compound 1) and Ac-Gly-Asn-Tyr-NH2 (compound 2). The compounds are synthesised according to standard solid phase synthesis as described in WO01/62775. A further example of compounds useful in the invention is trans-resveratrol and CAPE (caffeic acid phenethyl ester). Methods for making the compounds have been described. See e.g, the PCT/DK01/00127 (WO 01/62775) and PCT/US02/05773 (WO 02/077017) applications.

EXAMPLE 2

Analysis of Metabolic Stress Induced by Glucose Removal

Cardiac arrhythmias can be caused by disturbances of both formation and conduction of the action potential. The propagation of an action potential from cell to cell is mediated by the intercellular gap junctions. These gap junctions consist of channels, which are built by specialised proteins called connexins. There are several lines of evidence showing that a reduced expression and/or a disturbed distribution of the connexins, can be deleterious for normal impulse propagation and thereby arrhythmogenic. One example is the alterations seen during and after ischemia. During acute ischemia uncoupling of the cells are mainly believed to be caused by intracellular acidification, increased intracellular Ca2+, reduced intracellular ATP and by elevated concentrations of long-chain acylcarnitines and fatty acids [1, 2]. After the acute phase of ischemia, remodelling occurs where the architecture of the infarcted area and its border zone is altered. This remodelling has been associated with areas of connexin disarray and the development of potential reentrant circuits, which are believed to act as arrhythmogenic substrates [3]. In vivo and in vitro studies have shown that a group of antiarrhythmic peptides can delay and inhibit the onset of arrhythmia, and subsequent studies have shown that these peptides increase the electrical coupling between cells [2].

A. Methods

1. Cell culture: In short the hearts from 20 neonate rats (age 1–2 days) are excised aseptically. The ventricles are isolated and cut into 4–6 pieces, which are digested in several steps in a Hanks buffered saline with trypsin and DNAse. The cells are then centrifuged and resuspended in MEM with 5% FCS. To eliminate non-muscle cells the suspension is preplated in petri dishes for 30 minutes at 37° C. The cells in suspension are then seeded onto collagen coated coverslips. Seeding density will be adjusted to give confluent cultures.

2. Electrophysiology: The cover slips with confluent cardiomyocytes are mounted in an open chamber on the stage of an inverted microscope and superfused with Dulbeccos phosphate buffered saline (PBS) by gravity driven flow at 1 ml/min, 37° C. The solution (PBS) contain (in mM): Na+ 152, K+ 4.2, Cl− 141.5, PO43− 9.5, Ca2+ 0.9, Mg2+ 0.5, pH 7.4. Patch clamp pipettes are pulled from 1.5 mm glass capillaries (GC150F-15, Harvard Apparatus) on a Sutter Flaming-Brown P-87 microelectrode puller and fire polished to a resistance of 4–6 MW. Pipettes are filled with an intracellular like solution containing in mM: K+ 150, Na+ 15, Cl− 5, Gluconate− 150.2, EGTA 5, HEPES 5, Ca2+ 2 mM, Mg2+ 1.6, pH 7.2.

The patch clamp set-up consists of a synchronised discontinuous amplifier (SEC-05LX, NPI electronics) and data is digitised using an INT-10 interface (NPI electronics) and a PC1200 data acquisition board (National Instruments). Both current and voltage signals are low pass filtered at 1 kHz using the internal filters of the amplifiers and digitised at 10 kHz.

A cell is approached with an electrode using a PatchMan 5173 micromanipulator (Eppendorf). When contact with the cell is obtained (seen as a sudden increase in input resistance), suction is applied until the Giga seal configuration is established. Then a brief pulse of suction is applied to break the membrane under the pipette. The amplifier is then put in the zero-current clamp mode to monitor the membrane potential.

Some distance (>>1 cm) away a bipolar platinum electrode is used to pace the culture. The delay between the stimulus artifact and the appearance of an action potential in the patched cell is then a measure of the conduction velocity.

The cells were perfused with control solution with 0.1 g/l BSA until a stable baseline in the stimulus-activation interval (SAI) was established. Then the perfusate was changed to solution without glucose for 15 minutes and subsequently challenged with compound 1 ($10^{-8}$ M) for 20 minutes. In parallel, control experiments were performed which were conducted on a similar timescale without adding compound 1. Date are expressed as percent change relative to baseline prior to removal of glucose from the media.

B. Results

As illustrated in FIG. 2, metabolic stress induced by removal of glucose produced a slight increase in the stimulus-activation interval suggesting that removal of glucose delayed the conduction velocity. In contrast, superfusion with a 10 nM concentration of compound 1 decreased the stimulus-activation interval, i.e. compound 1 increased conduction velocity in cultured primary cardiomyocytes. These data indicate that compound 1 increases cell-to-cell coupling in cardiomyocytes.

REFERENCES

[1] Carmeliet, E. Cardiac ionic currents and acute ischemia: from channels to arrhythmias. *Physiol Rev.*, 1999, 79: 917–1017.
[2] Dhein, S. *Cardiac gap junctions. Physiology, regulation, pathophysiology and pharmacology*. Karger, Basel, 1998.
[3] Peters, N. S. and Wit, A. L. Myocardial architecture and ventricular arrhythmogenesis. *Circulation*, 1998, 97: 1746–1754.

EXAMPLE 3

Immunoprecipitation and Analysis of Phosphorylated Connexins

Compounds used in this example were made using standard solid phase Fmoc chemistry. See the prior examples. Identification was performed by mass spectrometry, and the purity, determined by RP-HPLC. In situ binding and animal studies have shown that the following peptide (compound 1) binds to the receptor in the nano-molar range. Initial studies with compound 1 in 1 nM, 10 nM, 50 nM and 100 nM will determine whether studies with the following peptides compound 3 (H-GAG-4-Hyp-PY-NH2) and compound 4 (H-GNY-NH2) are conducted. These studies will also determine whether studies involving specific kinase inhibitors are conducted.

H9c2 cells were seeded in 24-multi well dishes in a density of 7,900 cells/cm$^2$ (~15,000 cells/well) and grown for 3 days in MEM suplemented with 10% foetal calf serum (FCS) and 1000 units penicillin/1000 μg streptomycin (pen/strep) in an atmosphere of 5% $CO_2$ and 100% humidity at 37° C.

The labelled cells were incubated in Triton X-100 lysis buffer (~5*10^7 cells/ml) for 1 hr at 4° C. The lysate is centrifuged 30 min at 20,000*g for 30 min. The supernatant was precleared by adding 10 ul Sepharose per 200 μl supernatant. The precleared supernatant were then added 0.5–1 μg phospho-tyrosine or phospho-serine antibodies (Sigma) and incubated for 1.5 hr at 4° C. in an orbital shaker. The antibody-complex was then captured by incubation with 50 μl of a 1:1 slurry of protein G Sepharose for 1.5 hr. Finally the complex were extensively washed with 0.1% (w/v) Triton X-100, 50 mM Tris, pH 7.4, 300 mM NaCl and 5 mM EDTA.

The complexes were loaded onto a 12% SDS gel and blotted onto a PVDF membrane. The membrane is blocked with 0.1% Tween 20, 50 mM Tris, pH 7.4, 300 mM NaCl, 5% dry milk (TBST) for minimum 2 h. The membrane was subsequently incubated with connexin 43 specific antibodies (Zymed) for 1.5 h at RT and developed with ECL+ (Amersham).

Figure 3A:
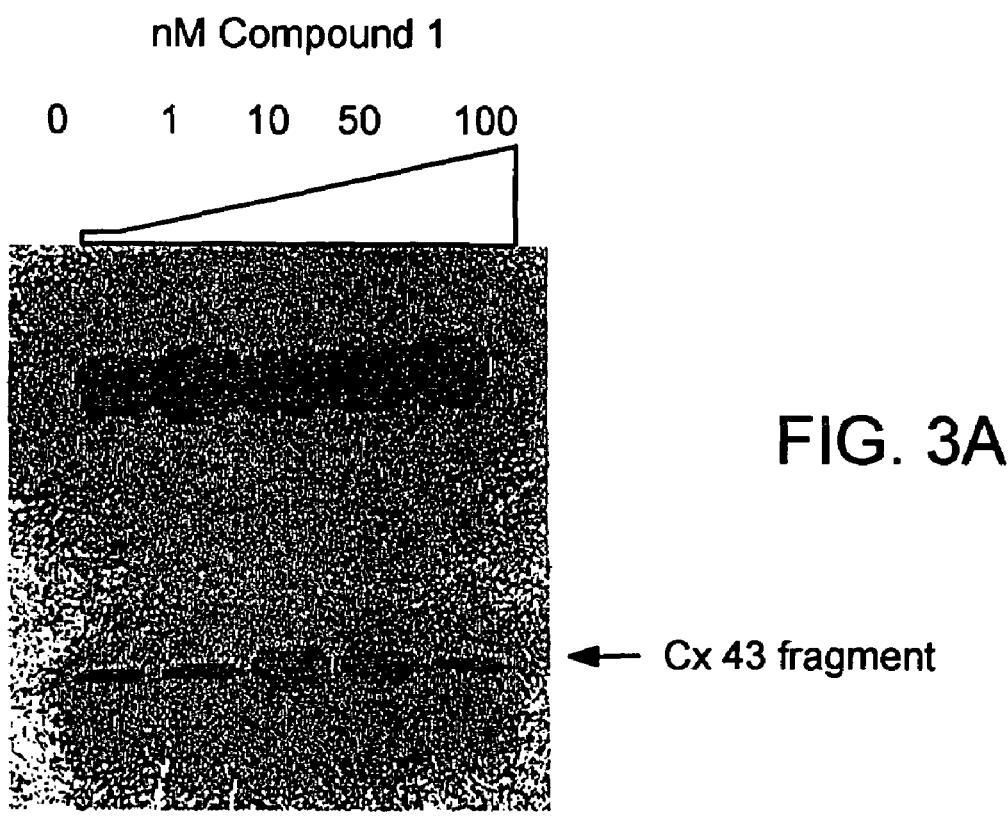
FIGS. 3A–B are representations of immunoblots showing detection of tyrosine phosphorylation in connexin 43 (Cx43).
Figure 3B:
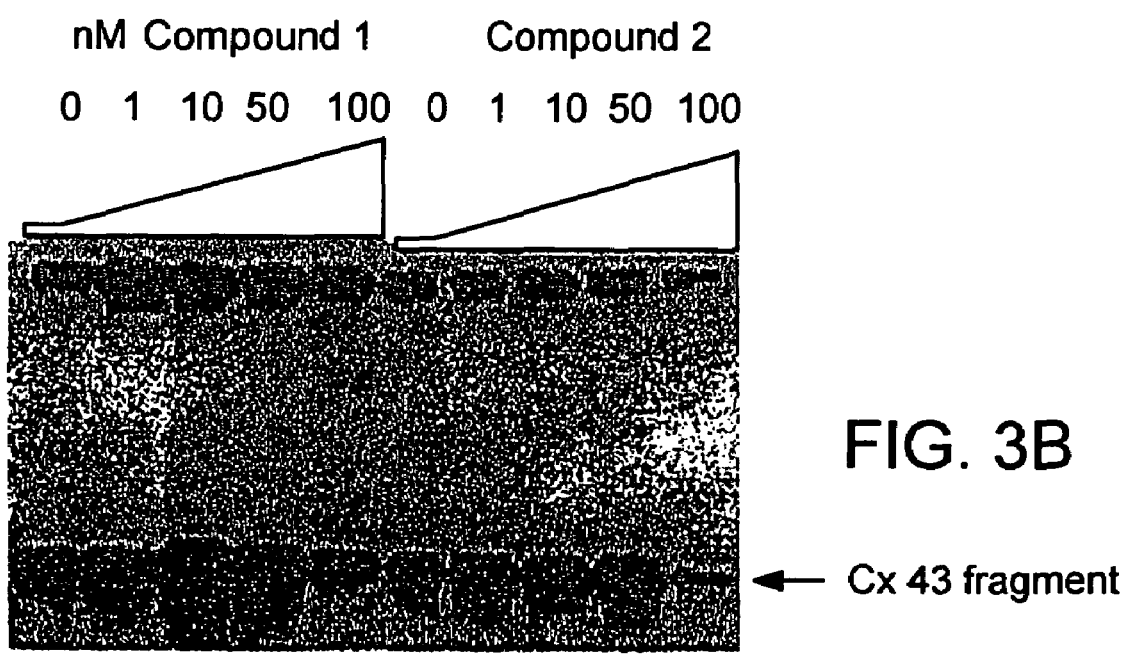

FIGS. 3A–B show immunoblots in which the anti-phosphotyrosine antibody was used. Cx43 fragment phosphorylation is depicted as a function of compound 1 (3A–B) and compound 2 (3B) concentration.

Figure 4A:
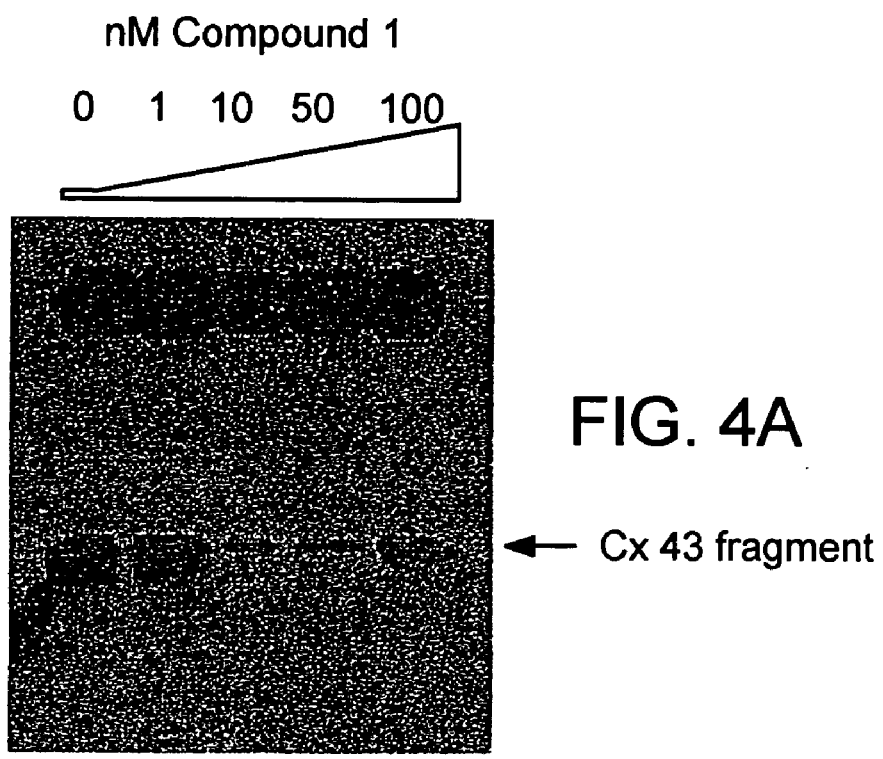
FIGS. 4A–B are representations of immunoblots showing detection of tyrosine phosphorylation (8A) and serine phosphorylation (8B) of Cx43.
Figure 4B:
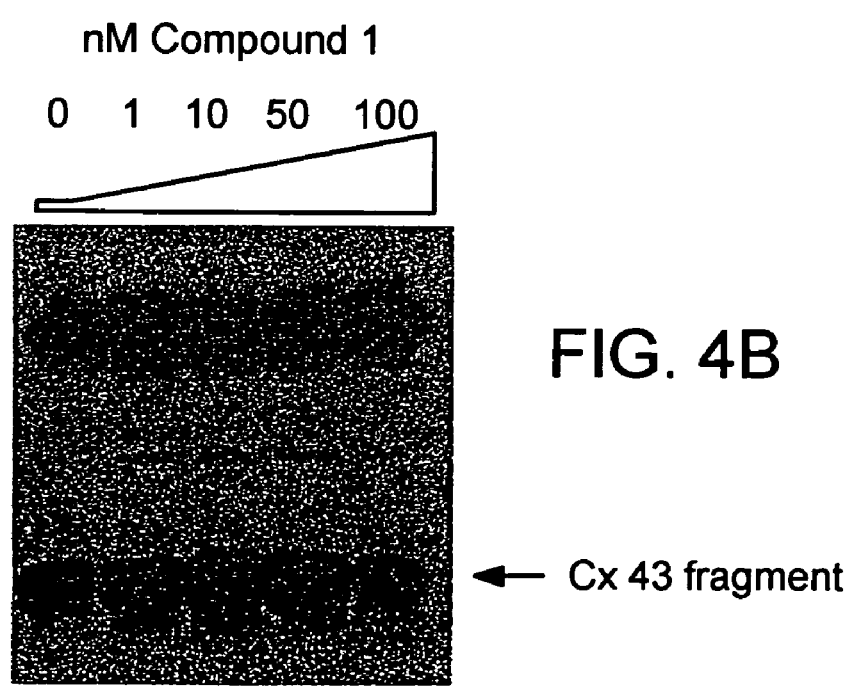

FIGS. 4A–B show immunoblots in which the anti-phosphoserine antibody (4A) or the anti-phosphotyrosine (4B) antibody was used.

EXAMPLE 4

Effect of Compound 1 Peptide on Hemichannel Activity in Confluent Cardiac Myocytes 1. Cell culture: Briefly, the hearts from 20 neonate rats (age 1–2 days) were excised aseptically. The ventricles were isolated and cut into 4–6 pieces, which are digested in several steps in a Hanks buffered saline with trypsin and DNAse. The cells were then centrifuged and resuspended in MEM with 5% FCS. To eliminate non-muscle cells the suspension was preplated in petri dishes for 30 minutes at 37° C. The cells in suspesion were then seeded onto collagen coated coverslips.

2. Dye-uptake: The cover slips with cardiomyocytes were incubated for 30 minutes with control solution (PBS) containing in mM: $Na^+$ 152, $K^+$ 4.2, $Cl^-$ 141.5, $PO_4^{3-}$ 9.5, $Ca^{2+}$ 0.9, $Mg^{2+}$ 0.5, glucose 6, pH 7.4. or an ischmia mimicking (injury) solution (as control only $K^+$ 8.2, no glucose, 10 mM deoxy-glucose, pH 6.5), both solutions containing 200 μM calcein. Then the cells were washed for 10 minutes with control solution.

The cover slips were mounted in an open chamber on the stage of an inverted microscope. Ten random fields were chosen and from each field three cells were chosen under conventional light microscopy. Then the cells were excited by 480 nm light and the fluorescence emmision measured at 510 nm, where the emission intensity is a measure of dye-uptake.

The effect of the compound 1 on dye-uptake was investigated under two conditions:

Experiment 1: In this series of experiments the cells were be incubated with control solution with calcein for 30 minutes and washed for 10 minutes without dye. In paired experiments the same experiment was performed where the peptide is added during the 30 minutes incubation.

Experiment 2: As experiment 1 only performed with injury solution instead of control solution.

3. Results Experiments using uptake of calcein in cultured cardiomyocytes from neonate rats show that the dye uptake is 38% higher than in control cells, when the cells are exposed to metabolic stress (in the form of low pH, increased extracellular $K^+$ and deoxyglucose 5–10 mM). This effect could be significantly reduced to 5% when the cells were co-incubated with compound 1 (10 nM, P<0.017 in paired t-test versus cells exposed to deoxyglucose alone, n=6). These results show that the increased membrane permeability through connexin hemi-channels seen after metabolic stress can be inhibited by compound 1. It is likely that this effect will be beneficial for cellular function and survival. Furthermore, phosphorylation experiments on cultured H9c2 cardiomyocytes have shown that compound 1 mediates tyrosine phosphorylation of connexin 43. Moreover, Cardiomyocytes exposed for 4 h with 0, 1, 10, 50 and 100 nM compound 1 an increase connexin 43 tyrosine phosphorylation. Tyrosine phosphorylation has been reported to mediate a disruption of gap junction intercellular communication and could easily explain the decrease in membrane permeability seen in the calcein experiments. In some experiments, the compound 1 was found to decrease Ser-phosphorylation.

Figure 5:
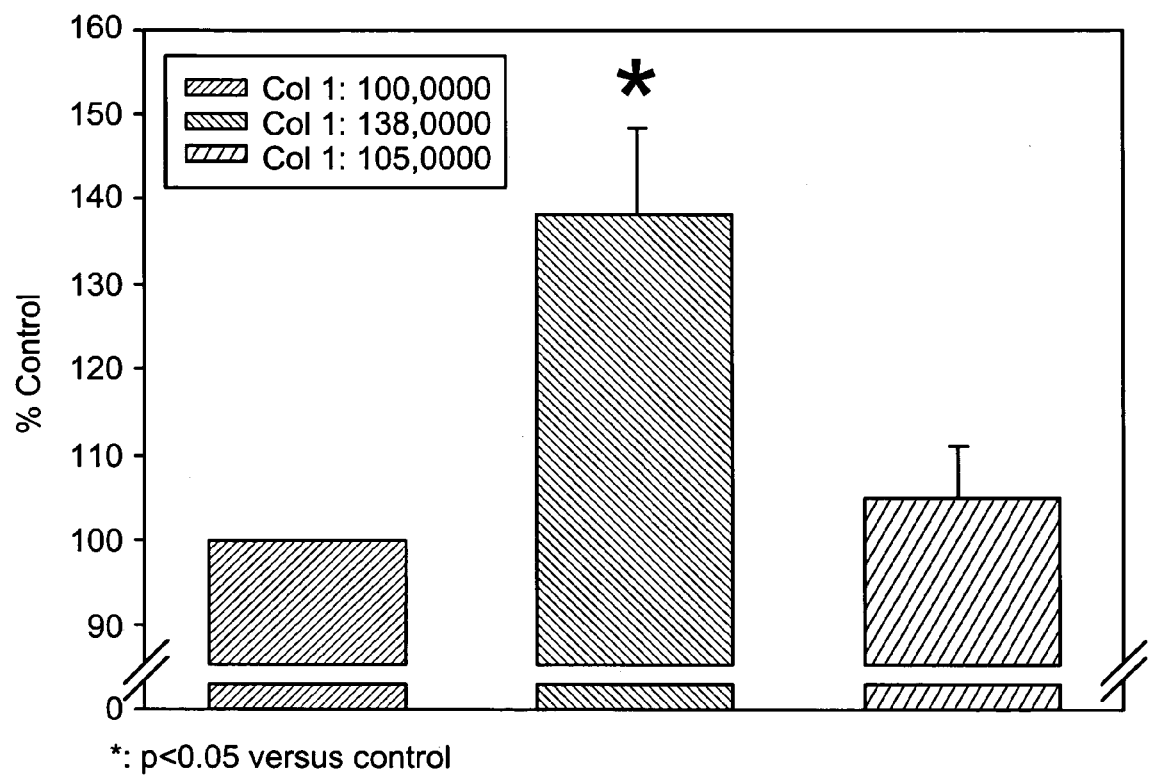
FIG. 5 is a graph showing effect of 10 nM compound 1 on ischemia-induced uptake of calcein in cultured cardiomyocytes.

FIG. 5 shows effects of 10 nM compound 1 on ischemia-induced uptake of the calcein in the cultured cardiomyocytes.

EXAMPLE 5

ELISA Assay of Site-specific Connexin Phosphorylation

An ELISA sandwich assay has been developed which enables measurements of site-specific phosphorylation of connexins in tissue samples as well as in cell cultures in a multi-well format (24–96 wells). Wells are coated with antibody (capture antibody) against the connexin type in question. Cell or tissue extracts are then reacted with capture antibody-coated plates at 4° C. o/n. The captured connexins that are phosphorylated are detected with an antibody directed against specific phosphorylation sites and conjugated with either biotin, FITC, TRITC or peroxidase.

The amounts of antibody bound to the specific phosphorylation sites may alternatively be measured with a radioactive labelled or an enzyme conjugated antibody against the species IgG of the detection antibody.

The principle has been demonstrated using mouse antiCx43 as capture antibody, rabbit anti-Tyr-P (tyrosine phosphorylation site) as detection antibody and anti-rabbit IgG either labelled with $^{125}$I or HRP (horse radish peroxidase) to measure the amounts of bound anti-Tyr-P. The principle may also be demonstrated using rabbit antiCx43 (5 μg/ml; cat. no. 710700, Zymed Lab. Inc., California, USA) as capture antibody, a monoclonal mouse anti-phosphotyrosine (50 μg/ml; cat. no. P-3300, clone pt66, Sigma, MO, USA) as detection antibody and anti-mouse whole antibody either labelled with $^{125}$I (sheep anti-mouse Ig cat. no. IM 131, Amersham Biosciences, Wales, UK) or peroxidase (donkey anti-mouse Ig; cat. no. 715-035-151) to measure the amounts of bound anti-phosphotyrosine.

Figure 6A:
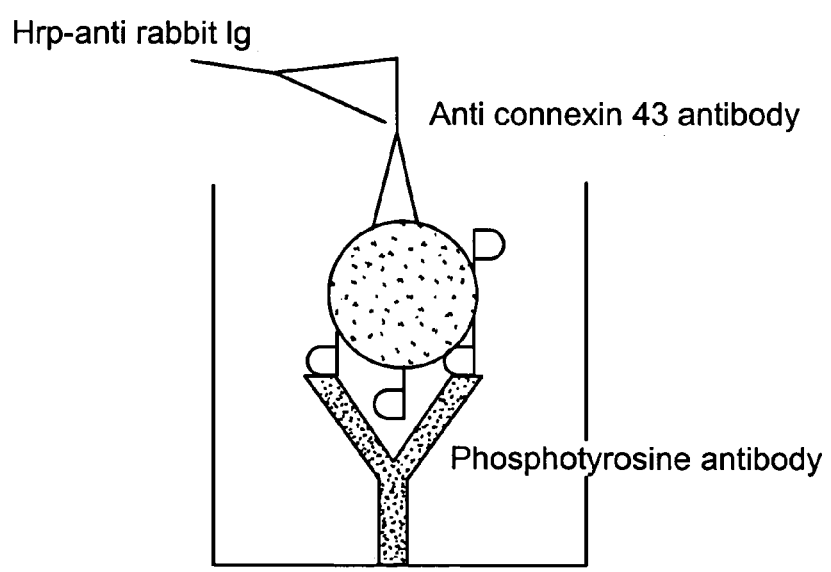
FIG. 6A is a drawing showing a preferred ELISA assay format.
Figure 6B:
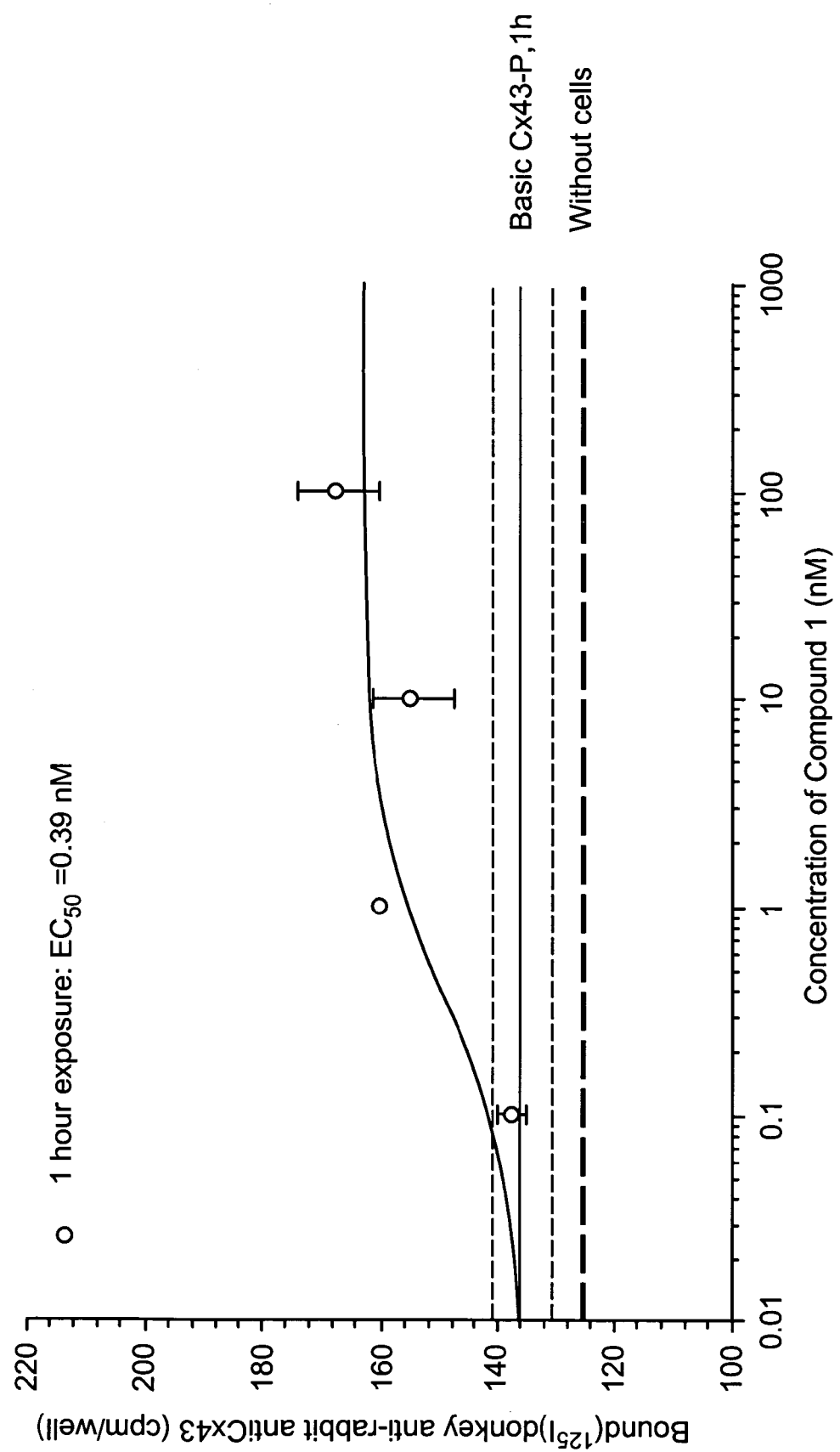
FIG. 6B is a graph showing ELISA results of phosphorylated Cx43 at Tyr-P in HeLa cells.
Figure 6C:
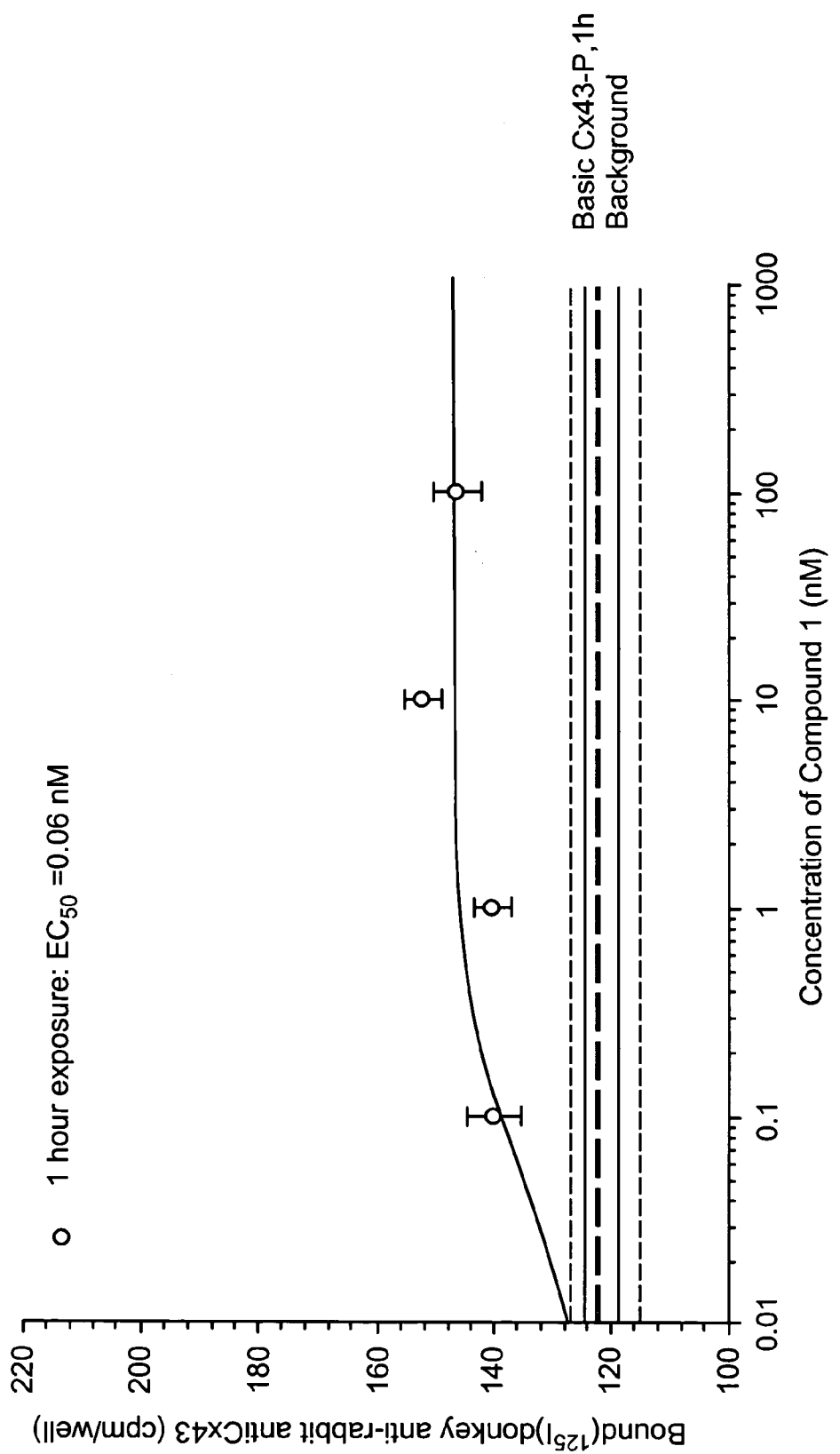
FIG. 6C is a graph illustrating ELISA results of phosphorylated Cx43 at Tyr-P in CHO cells.

FIG. 6A shows in schematic form a preferred ELISA detection format. FIGS. 6B and 6C show results of this example.

The present example and discussion provides evidence that metabolic strees opens connexin hemi-channels in cardiac cells, and that this opening can be circumvented by incubation with compound 1. Moreover, Examples 2–5 show that compound 1 closes hemichannels during metabolic stress. In agreement with the inhibitory effect of compound 1 on calcein uptake by hemichannels, i.e. a closing of hemichannels, the Examples also show that compound 1 assists in modulating the tyrosine phosphorylation state of connexin 43. Compound 1 is known to open gap junctions, cf. WO01/62775 and it is known that the inhibition of dephosphorylation of connexins prevents closing of gap junction channels. Thus, it is believed that compounds provided herein which can be shown to have beneficial gap junction opening or modulating effect of compound 1, i.e. all antiarrhythmic peptides disclosed in WO01/62775 and known peptides such as AAP, AAP10, HP5 and the like are useful in the present invention as modulators of hemichannel opening or closing. It is also believed that compound 1 maintains or increases the tyrosine phosphorylation of Cx43, thereby modulating hemichannel function.

EXAMPLE 6

Dye Uptake in Cardiomyocytes

1. Methods Ventricular myocytes were isolated from neonate rats by trypsin digestion and plated onto collagen-coated cover slips. After four days the myocytes formed confluent and synchronously beating sheets of cells. To measure dye uptake, cells were incubated in buffer containing 200 µM calcein for 30 minutes at room temperature. Then coverslips were thoroughly washed with control buffer and mounted in an open bath chamber and superfused with control buffer (RT). Cells were excited with 480 nm light by means of a Xenon lamp and a monochromator. Images of the fluorescence emitted at 510 nm were collected by a cooled CCD camera (Sensicam). Excitation control and image acquisition was controlled using Imaging workbench (Axon).

Under light microscopy three regions were placed over cardiomyocytes in an image. Then average fluorescence intensity was measured, and the procedure was repeated until 30 regions in 10 images had been measured. The average of these measurements were used as value for the given experimental condition, that is n=1. In each series one control incubation was performed and all experimental values are given as relative to this value.

Solutions: Control buffer (in mM): NaCl 136, KCl 4, $MgCl_2$ 0.8, $CaCl_2$ 1.8 HEPES 5, MES 5, Glucose 6, pH 7.3 Stress buffer (in mM): NaCl 136, KCl 8, $MgCl_2$ 0.8, $CaCl_2$ 1.8 HEPES 5, MES 5, Deoxy-glucose 10, pH 6.2

Figure 7C:
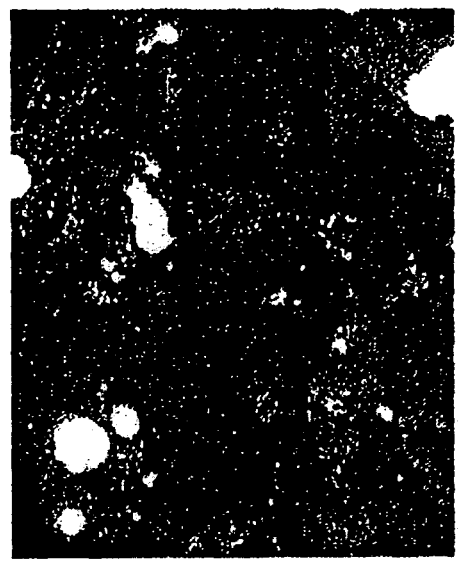
FIG. 7A–C are photomicrographs showing dye uptake in cultured cardiomyocytes.
Figure 7B:
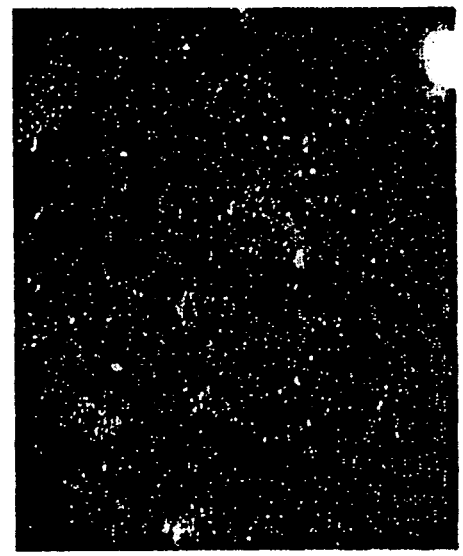
Figure 7A:
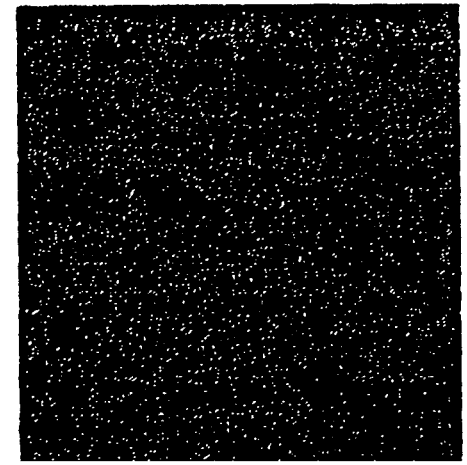

2. Results Incubation of cells with calcein under control condition gave some fluorescence staining, which was mostly of a localized particulate nature (see FIG. 7A-C, panel B). On top of the cultured myocytes, curled up cells that immediately stained with trypan blue, were often found. These cells stained heavily with calcein and care was always taken not to place the regions of measurements over these cells. When cells were exposed to metabolic inhibition the pattern of staining changed, and diffuse staining throughout the cytosol was observed (FIG. 7C). The average intensity during stress was 36.2±4.18% higher compared to control (n=5, P<0.001 in paired t-test).

Figure 8:
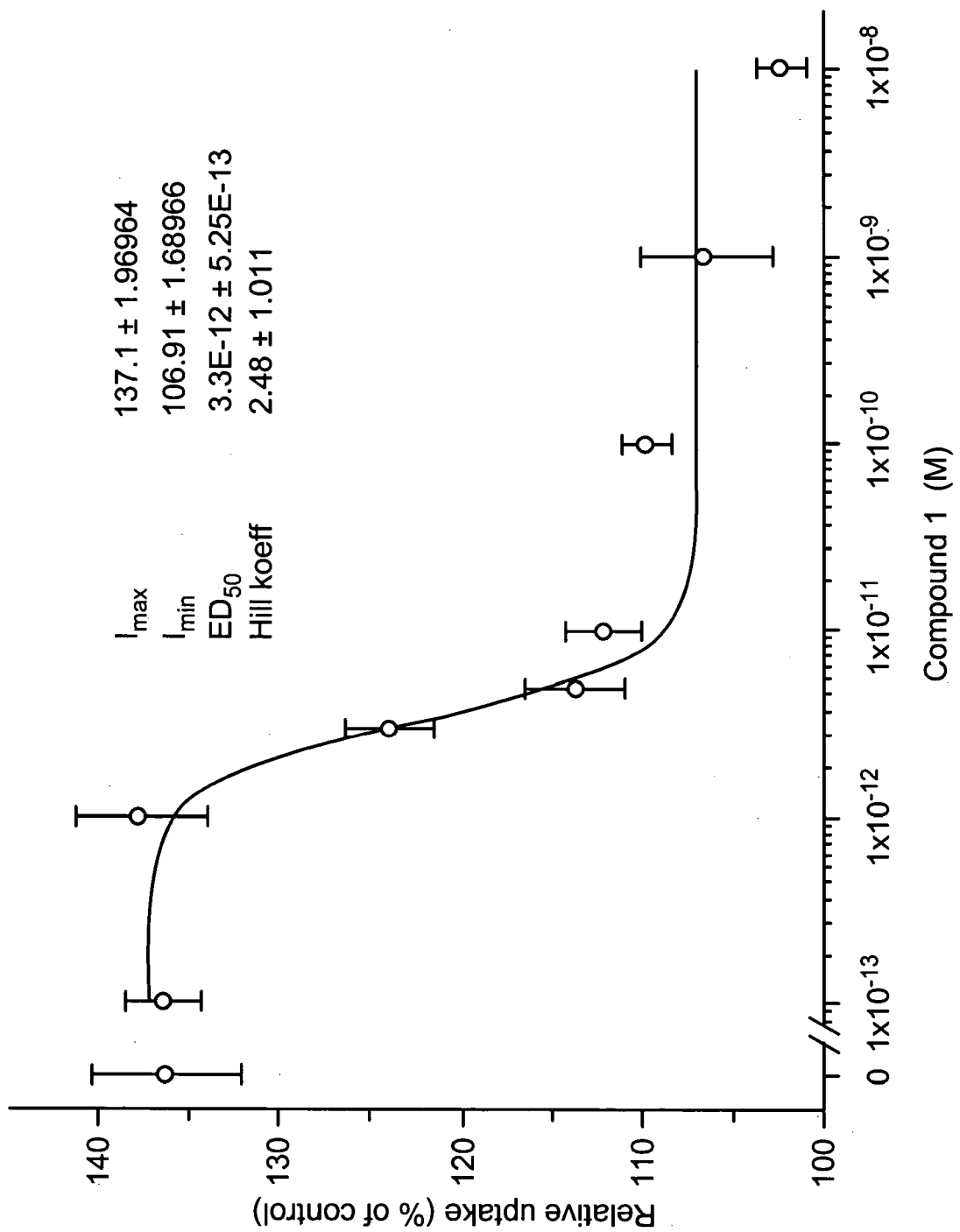
FIG. 8 is a graph showing that compound 1 reduces stress-induced calcein uptake in a dose-dependent manner.

This confirms findings in cardiac and other cell types, that metabolic inhibition activates the uptake of fluorescent dyes, probably via connexin hemi-channels. We hypothesized that one of the mechanisms by which the AAP family of peptides could exert its positive effects on cardiac tissue, could be to interrupt activation of hemi-channels, thereby improving cellular homeostasis. To investigate this, cells were exposed to stress in the presence of ZP123 in concentrations between 0.1 pM and 10 nM. The results are presented in FIG. 8, where each data point represent 5 experiments. As can be seen ZP123 dose-dependently reduced the uptake of calcein. Using a sigmoidal function $ED_{50}$ was estimated to 3.3±5.3 pM with a Hill coefficient of 2.5±1.0. Average intensity during maximal inhibition by compound 1 was 6.9±1.7% above control.

EXAMPLE 7

Volume Measurements in Cardiomyocytes

1. Methods: Ventricular myocytes were isolated from neonate rats by trypsin digestion and plated onto collagen-coated cover slips. After four days the myocytes formed confluent and synchronously beating sheets of cells. To measure cell volume cells were loaded with calcein-AM (5 µM in control buffer) for 15 minutes at 37° C. and the cover slips mounted in an open bath chamber. The following experiments were performed at room temperature. Using a Leica laser confocal microscope, an optical cross-section was performed every 20 seconds throughout the duration of the experiments.

The optical cross-sections were analyzed using Metamorph (Universal Imaging). The area of the cell was determined as the area of pixels with fluorescence intensities higher than a threshold value chosen to minimize background induced fluctuations. Data are presented as relative volumes by dividing each value by the average area under control conditions (the last measurement before metabolic stress).

Solutions: Control buffer (in mM): NaCl 136, KCl 4, $MgCl_2$ 0.8, $CaCl_2$ 1.8 HEPES 5, MES 5, Glucose 6, pH 7.3 Stress buffer (in mM): NaCl 136, KCl 8, $MgCl_2$ 0.8, $CaCl_2$ 1.8 HEPES 5, MES 5, Deoxy-glucose 10, pH 6.2

Figure 9B:
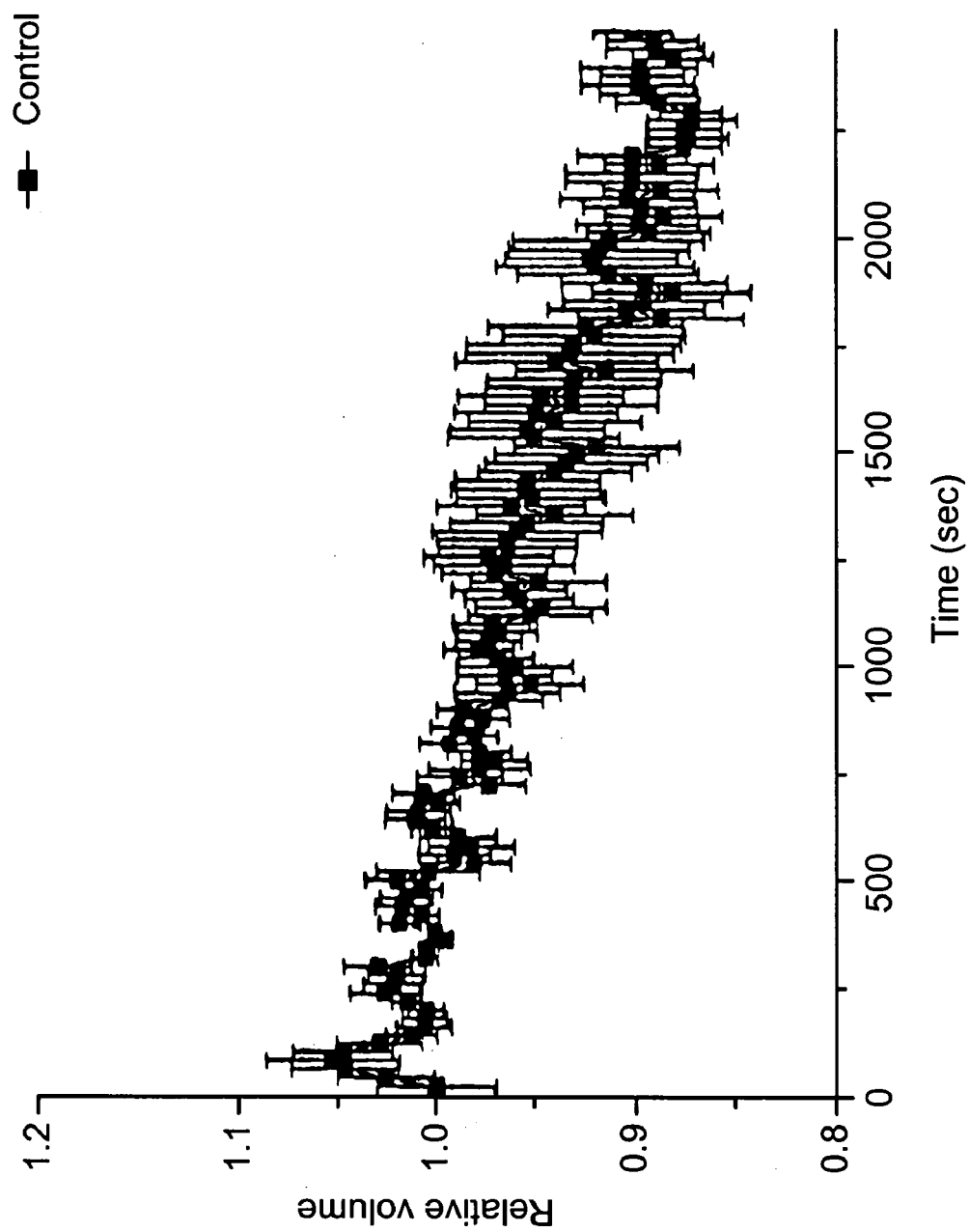

2. Results Under control conditions cells on average tended to slightly decrease their volume with time (FIG. 9B shows average data from 5 experiments). When cells were challenged with metabolic inhibition, the fall in volume was reversed to a net-increase (filled squares in FIG. 9A). On average the relative volume was 1.06±0.02 (last five minutes of stress, n=5), whereas the volume of control cells in this period was 0.94±0.04.

Dye uptake measurements in myocytes have shown that compound 1 inhibits open connexin hemi-channels. It is believed that the hemi-channels might contribute to the observed swelling. To test this compound 1 (0.1 nM) was included in the stress medium and volume monitored. Data from six experiments are shown in FIG. 9A (open squares) and as can be seen the stress induced swelling was prevented. Average relative volume during stress in the presence of compound 1 was 0.93±0.05.

Figure 10:
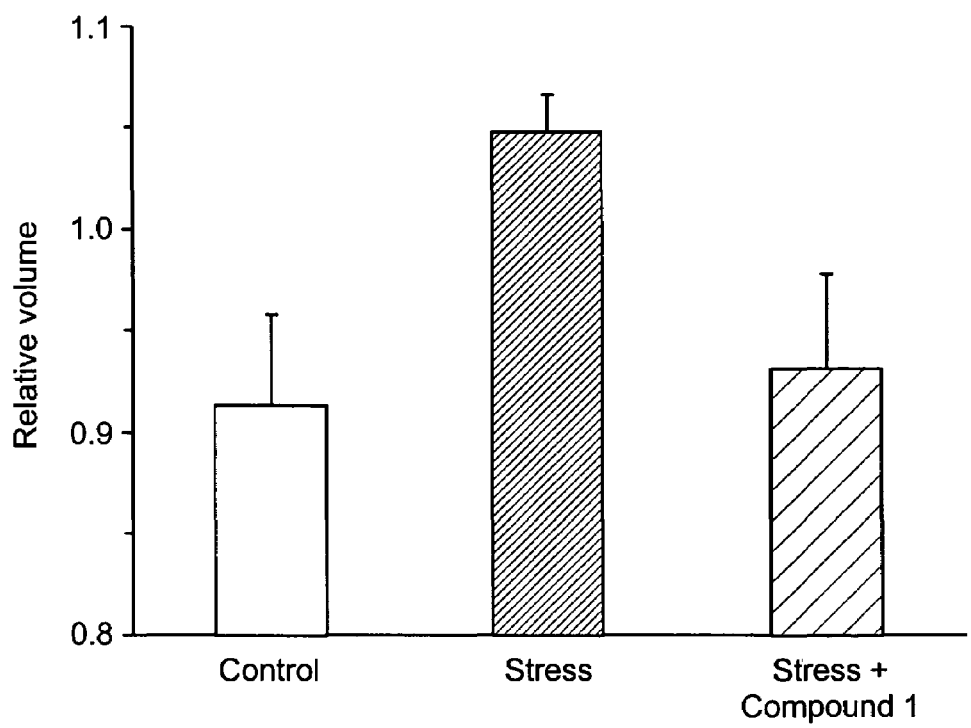
FIG. 10 is a graph showing effect of compound 1 (0.1 nM) on stress-induced cell swelling.

When comparing data from control, stress and stress plus compound 1 using a one-way ANOVA, significant differences were detected (see FIG. 10). Post.hoc. testing (LSD) showed that stress was significantly different from control (P<0.05) and stress plus compound 1 (P<0.05), whereas control was not different from stress plus compound 1 (P>0.76).

EXAMPLE 8

Reduction of Infarct Size After Myocardial Infarction in Rats

1. Methods:

Male Lewis rats (300–350 g; M&B, Ll. Skendsved, Denmark) were anaesthetized with a neurolept anaesthesic combination (Hypnorm® (fentanyl citrate 0.315 mg/ml and fluanisone 10 mg/ml)+midazolam (5 mg/ml)). Commercial solution of midazolam was diluted 1:2 in distilled water. Three parts of the diluted midazolam is mixed with one part hypnorm®. Anesthesia was induced by s.c. administration of 0.2 ml of this solution per 100 gram rat. When surgical anesthesia was established, an endotracheal cannula is inserted and the animal is artificially ventilated using a Harvard rodent ventilator adjusted to maintain arterial pH at 7.3–7.5 during surgery.

Compound 1 was delivered by an osmotic minipump (Alzet model 2ML4) that was inserted into the intraperitoneal (i.p.) cavity immediately prior to induction of the myocardial infarction. The pump was filled with vehicle (isotonic saline) or Compound 1 and primed at 37° C. for 24 hours prior to the operation. In order to ensure that the therapeutic plasma concentration was obtained already at the time of infarction, a loading dose of Compound 1 was given s.c. prior to ligation of the LAD. With the s.c. loading dose, a steady-state plasma level was reached already after 3 min.

After administration of the s.c. loading dose of Compound 1 and after i.p. insertion of the osmotic minipump, a left thoracotomy was performed, and the left anterior decending artery was ligated using a 6-0 silk suture. The thorax is closed in layers, and a negative pressure was induced in the pleural cavity to unfold the lungs. Sham-operated animals were subjected to the same procedure without ligation of the LAD. Postoperatively, the animal were allowed to recover in a heated cabinet at 30° C. with 50% oxygen until the next morning. To prevent dehydration during the recovery period, the rat was given 5 ml 5% glucose s.c. immediately after completion of surgery and another 5 ml 5% glucose at 4 p.m. To relieve postoperative pain, the rat was treated with buprenorphine (20 µg/100 g s.c. b.i.d.) and meloxicam (0.1 mg/100 g s.c. once daily) for three days after the myocardial infarction. In this study the infusion dose given to rats with myocardial infarction (MI) was adjusted to produce plasma concentrations at 0 [vehicle=isotonic saline], 1.7±0.4 nM [dose 1], 5.7±0.4 [dose 2], or 93.7±12.3 nM [dose 3]. Plasma concentrations of Compound 1 were measured by mass spectrometry following solid phase extraction. Doses used are shown below in Table I:

TABLE I

| Group | Plasma concentration after 3 weeks nM | S.c. loading dose of Compound 1 (nmol/kg) | I.p. infusion dose of Compound 1 (pmol/kg/min) |
|---|---|---|---|
| Sham-MI | 0 | 0 | 0 |
| MI | 0 | 0 | 0 |
| MI | 1.7 ± 0.4 | 0.25 | 11 |
| MI | 5.7 ± 0.4 | 2.5 | 110 |
| MI | 93.7 ± 12.3 | 25 | 1100 |

Three weeks after ligation of LAD, the rats were anesthetized with an i.p, injection of pentobarbital (50 mg/kg). The animals were placed on a heating blanket in order to maintain body temperature at 37° C. Tracheotomy was performed and the rat was ventilated with oxygen using a Harvard rodent ventilator. The ventilator was adjusted to maintain arterial pH at 7.35–7.45. PE50 catheters were placed in the femoral vein and artery for i.v. administration and arterial pressure measurements, respectively. After insertion of the femoral i.v. catheter, the animal was paralysed by i.v. administration of pancuronium, 1 mg/kg. Anaesthesia and respiratory paralysis is maintained by continuous i.v. infusion of pentobarbital (2.5 mg/kg/h) and pancuronium (1 mg/kg/h) delivered in isotonic saline (50 µl/min). A tygon catheter was inserted into the left ventricle via the right carotid artery for determination of left ventricular end-diastolic pressure. After recording of left ventricular end-diastolic pressure (LVEDP), The hearts are removed from the bodies by cutting the veins and arteries a few mm from the hearts. The hearts were carefully rinsed for blood with isotonic saline, weighed and placed in 4% neutral buffered formalin.

After fixation the large vessels were cut close to the heart. Thereafter the hearts were cut into parallel slices with a thickness of 1.5 mm using an aggregate consisting of parallel razor blades with a distance of 1.5 mm. The slices are perpendicular to the long axis of the heart.

The slices were placed in two histological capsules so that the first slice is placed in one of the capsules by random number and the second in the other, the third in the first capsule and so on. After embedding, the slices were cut into 4 µm thick sections that are stained by Hematoxylin-eosin and by Masson-trichrome.

Using a microscope with a stage that can be moved in predetermined steps, both Masson-trichrome stained slides were examined and the number of points hitting fibrous tissue (blue stained in Masson-trichrome) and normal tissue are counted. The microscope was connected to a video camera and the image is displayed on a screen. The morphometry system used was Cast2 from Olympus, Denmark. Infarct size was calculated as % fibrous tissue in the heart.

Figure 11:
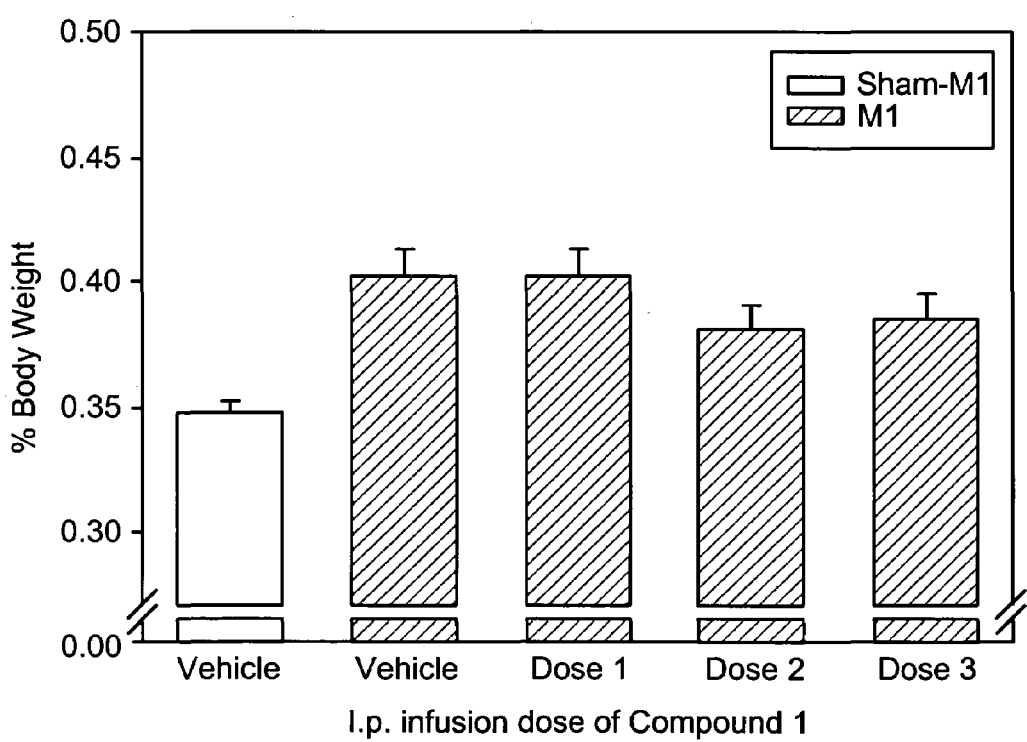
FIG. 11 is a graph showing a reduction in heart weight to body weight ratio after administration of Compound 1 to rats subjected to myocardial infarction.

2. Results:

As illustrated in FIG. 11, the heart weight-body weight ratio was reduced by the two highest doses of Compound 1 suggesting that the compound reduces the hypertrophic consequences (i.e., remodelling) of myocardial infarction.

Figure 12:
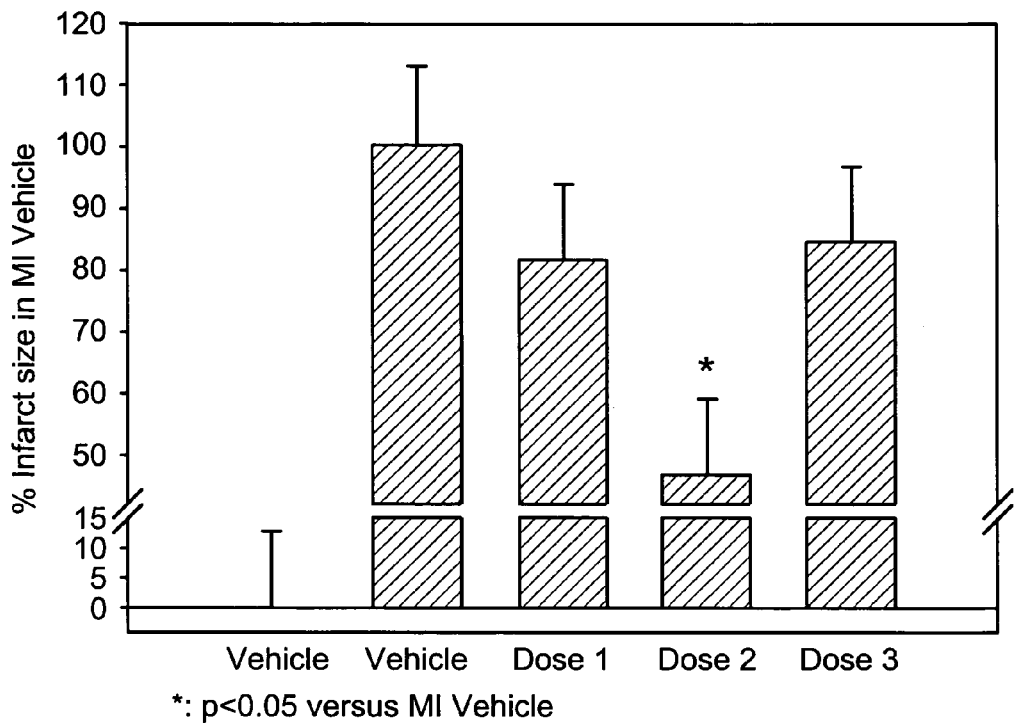
FIG. 12 is a graph showing a reduction in infarct size in rats following administration of Compound 1.

As shown in FIG. 12, treatment with Compound 1 for three weeks reduced infarct size by 20–50% relative to infarct size in rats subjected to a myocardial infarction, but treated with vehicle. Tyhis indicates that Compound 1 has cytoprotective actions during myocardial ischemia. In line with what has been described herein, these data indicate that Compound 1 reduces the size of the myocardial infarct by a mechanism that may involve prevention of cell swelling. Thus, prevention of cell swelling may prevent compression of surrounding healthy tissue, and therefore prevent compression of the microcirculation in surrounding healthy tissue. Therefore, in this application we claim that this principle may prevent the consequence of any ischemic lesion in any organ, preferably but not limited to organs with a confined fibrous capsule (e.g., heart, kidney) or organs surrounded by bone (e.g., brain, spinal cord, bone marrow).

Figure 13:
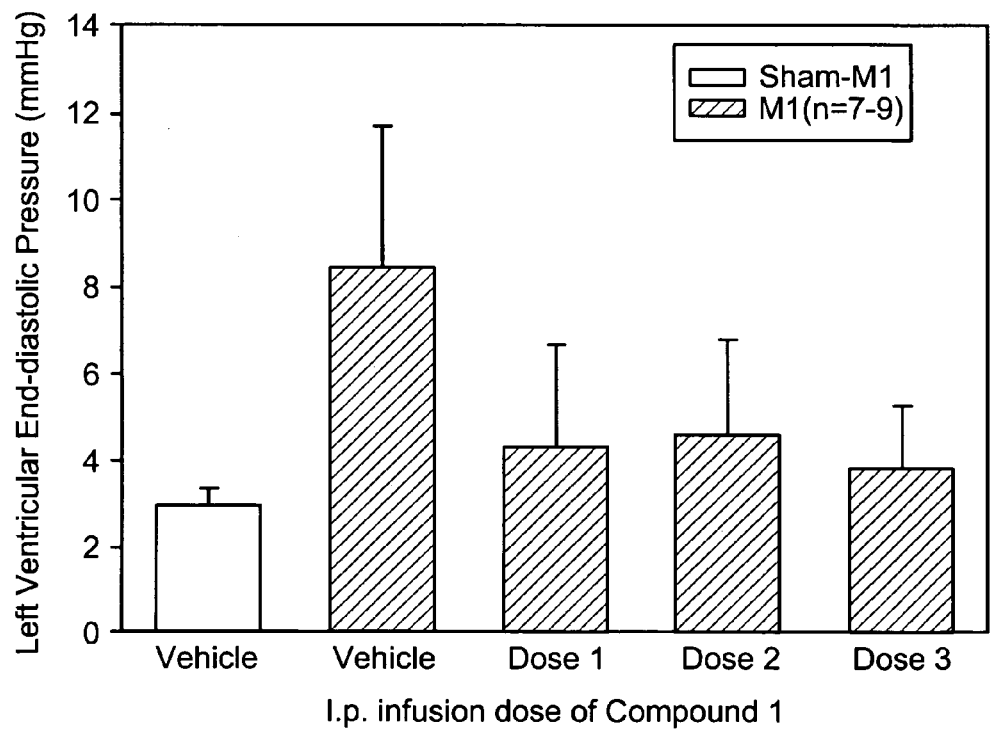
FIG. 13 is a graph showing improved cardiac function after administration of Compound 1 to rats subjected to myocardial infarction.

As shown in FIG. 13, rats subjected to myocardial infarction but treated with either dose of Compound 1 for three weeks, had better an improved cardiac function with less congestion in the left ventricle as demonstrated by a reduced left ventricular end-diastolic pressure. This data indicate that Compound 1, prevents the impairment of cardiac function following a myocardial infarction.

All references disclosed herein are incorporated by reference. The invention has been described with reference to preferred embodiments thereof. However, it will be appreciated that those skilled in the art, upon consideration of this disclosure, may make modifications and improvements within the spirit and scope of the invention.

What is claimed is:

1. A method of modulating a hemichannel in a cell, tissue or organ exposed to stress, the method comprising contacting the stressed cell, tissue or organ with a therapeutically effective amount of at least one compound selected from the group consisting of compounds represented as Formula I or II, wherein the contact is sufficient to modulate the hemichannel in the stressed cell, tissue or organ, wherein Formula I is defined as follows:

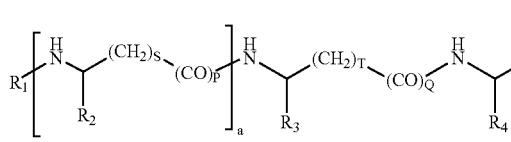

(I)

wherein $R_1$ represents H or acetyl (Ac)

$R_2$ represents a sidechain of one of the amino acids Gly, Tyr, D-Tyr, Phe and D-Phe, $R_3$ represents any amino acid sidechain, $R_4$ represents a sidechain of one of the amino acids Gly, Tyr, D-Tyr, Phe and D-Phe, $R_5$ represents OH or $NH_2$, and a, S, T, P and Q are integers and independently=0 or 1;

and salts thereof, and wherein Formula II is defined as follows:

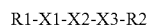

wherein,

X1 is 0, Ala, Gly, β-Ala, Tyr, D-Tyr, Asp,

X2 is 0, Ala-Gly-T4c-Pro, Ala-Sar-Hyp-Pro, Ala-Asn, D-Asn-D-Ala, D-Asn, Gly, Ala, D-Ala, β-Ala, Asn or,

X3 is Tyr, D-Tyr, Gly or Phe, and

R1 is H or Ac,

R2 is OH or $NH_2$, with the proviso that X1 and X2 are not both 0; and salts thereof.

2. The method of claim 1, wherein the modulating of the hemichannel is selected from the group comprising closing the hemichannel and opening the hemichannel.

3. The method of claim 2, wherein the method further comprises phosphorylating a tyrosine residue of connexin 43 (Cx 43) and closing the hemichannel.

4. The method of claim 2, wherein the method further comprises dephosphorylating a serine residue of connexin 43 (Cx 43) and opening the hemichannel.

* * * * *

```
                            SEQUENCE LISTING

<160> NUMBER OF SEQ ID NOS: 11

<210> SEQ ID NO 1
<211> LENGTH: 147
<212> TYPE: PRT
<213> ORGANISM: Rattus norvegicus

<400> SEQUENCE: 1

Val Lys Asp Arg Val Lys Gly Arg Ser Asp Pro Tyr His Ala Thr Thr
 1               5                  10                  15

Gly Pro Leu Ser Pro Ser Lys Asp Cys Gly Ser Pro Lys Tyr Ala Tyr
                20                  25                  30

Phe Asn Gly Cys Ser Ser Pro Thr Ala Pro Leu Ser Pro Met Ser Pro
            35                  40                  45

Pro Gly Tyr Lys Leu Val Thr Gly Asp Arg Asn Asn Ser Ser Cys Arg
        50                  55                  60

Asn Tyr Asn Lys Gln Ala Ser Glu Gln Asn Trp Ala Asn Tyr Ser Ala
 65                  70                  75                  80

Glu Gln Asn Arg Met Gly Gln Ala Gly Ser Thr Ile Ser Asn Ser His
                85                  90                  95

Ala Gln Pro Phe Asp Phe Pro Asp Asp Asn Gln Asn Ala Lys Lys Val
            100                 105                 110

Ala Ala Gly His Glu Leu Gln Pro Leu Ala Ile Val Asp Gln Arg Pro
        115                 120                 125

Ser Ser Arg Ala Ser Ser Arg Ala Ser Ser Arg Pro Arg Pro Asp Asp
    130                 135                 140

Leu Glu Ile
145

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Ala Asn Tyr
      1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions, R-groups and preferred embodiments

<400> SEQUENCE: 3

Gly Gly Tyr Tyr
  1
```

```
<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dab
<220> FEATURE:
<221> NAME/KEY: MOD_RES
<222> LOCATION: (4)
<223> OTHER INFORMATION: Hyp

<400> SEQUENCE: 4

Gly Xaa Gly Xaa Pro Tyr
  1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dapa
<220> FEATURE:
<221> NAME/KEY: MOD_RES
<222> LOCATION: (4)
<223> OTHER INFORMATION: Hyp

<400> SEQUENCE: 5

Gly Xaa Gly Xaa Pro Tyr
  1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Hyp

<400> SEQUENCE: 6

Tyr Pro Xaa Gly Gln Gly
  1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Hyp

<400> SEQUENCE: 7

Tyr Pro Xaa Gly Asn Gly
  1               5
```

```
<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dab
<220> FEATURE:
<221> NAME/KEY: MOD_RES
<222> LOCATION: (5)
<223> OTHER INFORMATION: Hyp

<400> SEQUENCE: 8

Gly Xaa Ala Gly Xaa Pro Tyr
 1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Dapa
<220> FEATURE:
<221> NAME/KEY: MOD_RES
<222> LOCATION: (5)
<223> OTHER INFORMATION: Hyp

<400> SEQUENCE: 9

Gly Xaa Ala Gly Xaa Pro Tyr
 1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Hyp

<400> SEQUENCE: 10

Tyr Pro Xaa Gly Ala Gln Gly
 1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Hyp
```

```
<400> SEQUENCE: 11

Tyr Pro Xaa Gly Ala Asn Gly
  1               5
```